US012767964B2

(12) United States Patent
Zhang et al.

(10) Patent No.: US 12,767,964 B2
(45) Date of Patent: Oct. 20, 2026

(54) SYSTEMS, COMPOSITIONS, AND METHODS FOR BIOCATALYZED PRODUCTION OF A GREASE THICKENER

(71) Applicant: EXXONMOBIL TECHNOLOGY AND ENGINEERING COMPANY, Spring, TX (US)

(72) Inventors: Xiaozhou Zhang, Bridgewater, NJ (US); Jay Patel, Branchburg, NJ (US)

(73) Assignee: EXXONMOBIL TECHNOLOGY AND ENGINEERING COMPANY, Spring, TX (US)

( * ) Notice: Subject to any disclaimer, the term of this patent is extended or adjusted under 35 U.S.C. 154(b) by 266 days.

(21) Appl. No.: 18/651,609

(22) Filed: Apr. 30, 2024

(65) Prior Publication Data

US 2024/0368639 A1 Nov. 7, 2024

Related U.S. Application Data

(60) Provisional application No. 63/500,257, filed on May 4, 2023.

(51) Int. Cl.

*C12P 7/18* (2006.01)
*C12N 9/88* (2006.01)

(52) U.S. Cl.

CPC .................. *C12P 7/18* (2013.01); *C12N 9/88* (2013.01); *C12Y 402/01053* (2013.01)

(58) Field of Classification Search

CPC ...... C12P 7/18; C12N 9/88; C12Y 402/01053
See application file for complete search history.

(56) References Cited

U.S. PATENT DOCUMENTS 10,786,453 B2 * 9/2020 Deshayes ............ A61K 8/4973

* cited by examiner

*Primary Examiner* — Tekchand Saidha

(74) *Attorney, Agent, or Firm* — Vorys, Sater, Seymour and Pease, LLP

(57) ABSTRACT

Systems, methods, and compositions for biocatalyzed conversion of oleic acid to non-racemic (R)-10-hydroxystearic acid ((R)-10-HSA) are described herein. Some systems and methods may include mixing oleic acid, a buffer, and a surfactant to produce an emulsion. The emulsion may be mixed with recombinant enzyme produced by a transformed microorganism. The recombinant enzyme may biocatalytically convert oleic acid to (R)-10-HSA, which may be extracted from the emulsion via an organic solvent.

10 Claims, 8 Drawing Sheets

Specification includes a Sequence Listing.

| | V30p | H41R | F113W | S153A | T230M | C245A | S291T | M336L | T394K | L432P | S501A | K508A |
|---|---|---|---|---|---|---|---|---|---|---|---|---|
| MCC6 | X | | | | | | X | X | | X | | |
| MCC22 | | X | X | | | | | | | X | X | |
| MCC2 | | X | | | | | X | X | | X | | |
| MCC21 | | | | | | | | X | | X | | |
| MCC25 | | X | X | X | X | | X | X | | X | | |
| MCC8 | X | X | | X | | | | X | X | X | X | |
| MCC17 | | | | | | | | | X | X | | X |
| MCC19 | | X | X | | | | X | | X | X | | |
| MCC3 | X | | X | X | | | | | | X | X | |
| MCC9 | X | | X | | | | | | X | X | | X |
| MCC11 | | X | X | | | | | X | X | X | | X |
| MCC14 | | | | | | | | | X | | | |
| MCC15 | | | X | | X | | | X | | X | | |
| MCC18 | | X | X | X | X | | X | X | | X | | |
| MCC20 | | X | | | | | | | | X | | |
| MCC7 | | | X | | | | X | X | | X | | X |
| MCC12 | | | X | X | X | | X | | X | X | | X |

FIG. 4.

SYSTEMS, COMPOSITIONS, AND METHODS FOR BIOCATALYZED PRODUCTION OF A GREASE THICKENER

REFERENCE TO AN ELECTRONIC SEQUENCE LISTING

The contents of the electronic sequence listing (Sequence Listing.xml; Size: 78,799 bytes; and Date of Creation: Apr. 24, 2023) is expressly incorporated herein by reference in its entirety.

BACKGROUND

Greases often include a thickener. A common thickener that is used is Lithium (R)-12-hydroxystearate, which is manufactured from (R)-12-hydroxystearic acid ("R-12-HSA") and LiOH. Previous research has demonstrated that the chiral nature of thickener molecules (such as R-12-HSA) facilitates self-assembly of the thickener into twisted fibers that enhance the grease effectiveness as compared to racemic mixtures of a thickener. While industrial manufacturing techniques can be used to produce R-12-HSA, the output of these industrial techniques are commonly racemic. Accordingly, common manufacturing techniques often involve extracting R-12-HSA or other thickeners from natural biological sources (e.g., plants or seeds). However, the reliance on biological sources increases the impact of environmental changes, such as climate change, blight, or other crop disease vectors.

Some attempts have been made to produce thickeners equivalent to R-12-HSA. For example, German Application DE102019110921 describes the surprising performance of (R)-10-hydroxystearic acid ("(R)-10-HSA") as a grease thickener, amongst other things. U.S. Pat. No. 10,786,453 describes (R)-10-HSA's potential use as a component in cosmetics.

Additionally, attempts have been made to produce (R)-10-HSA using biocatalytic techniques. For example, Sun et al. describes the use of one oleate hydratase enzyme for the biocatalyzed production of (R)-10-HSA. Similarly, Chinese Patent No. CN112226428, Japanese Patent Application JP2017100988, and Korean Patent Application KR1020130126354 describe biocatalyzed production of (R)-10-HSA and its use as a food additive, an ingredient of cosmetic products, and the like.

SUMMARY

Aspects of the present disclosure relate to biocatalytic production of grease thickeners using recombinant enzymatic proteins (i.e., enzymes). Systems, methods, and compositions are disclosed that use one or more recombinant enzymes to convert oleic acid to non-racemic (R)-10-hydroxystearic acid ("(R)-10-HSA").

In contrast to conventional compositions, such as those describe above, the present compositions include a plurality of artificial intelligence-guided mutations from the wild type enzyme (e.g., oleic acid hydrate from bacterial strain *Paracoccus aminophilus*) that may catalyze conversion of oleic acid to a non-racemic (R)-10-HSA. The composition may be recombinant DNA, a portion of recombinant DNA inserted into a plasmid, or an assembly of amino acids. According to some examples and in comparison to the wild type enzyme the mutations may include, or may be translated into, one or more of: a proline at position 30; an arginine at position 41; a tryptophan at position 113; an alanine at position 153; a methionine at position 230; a threonine at position 291; a leucine at position 336; a lysine at position 394; a proline at position 432; an alanine at position 501; or an alanine at position 508.

Additionally and in contrast to conventional techniques, such as those described above, systems and methods are disclosed that leverage a recombinant enzyme to facilitate biocatalytic production of non-racemic (R)-10-HSA. For example, an emulsion may be formed by mixing oleic acid, a buffer, and a surfactant. One or more of the recombinant enzymes described herein are mixed with the emulsion to facilitate the conversion of the oleic acid to non-racemic (R)-10-HSA. The (R)-10-HSA can be extracted from the catalyzed mixture using one or more organic solvents (e.g., ethyl acetate, hexane, dichloromethane, benzene, acetone, and so forth). The systems and methods described herein may facilitate batch or continuous biocatalyzed production of non-racemic (R)-10-HSA.

DESCRIPTION OF FIGURES

The present systems, methods, and recombinant DNA and proteins for biocatalyzed production of a grease thickener are described in detail below with reference to the attached drawing figures, wherein:

FIG. 4 is a chart depicting selective amino acid substitution mutations for the recombinant oleic acid hydratase enzymes, in accordance with aspects described herein;

DETAILED DESCRIPTION

Biocatalysis provides an alternative to traditional chemical manufacturing techniques. Advantageously, biocatalysis can facilitate selective partial oxidation of medium- and long-chain hydrocarbons. For example, biocatalytic oxidations can achieve region- and stereo-selectivity that are not feasible with chemical catalysis. Accordingly, biocatalysis can facilitate the development and manufacturing of non-racemic mixtures of a thickener and some of the aspects described herein are directed to methods and processes for biocatalyzed production of non-racemic mixtures of one or more thickening agents.

A common thickener that is used is Lithium (Li) (R)-12-hydroxysterate, which is manufactured from (R)-12-hydroxystearic acid ("R-12-HSA") and LiOH. Although the hydroxyl group is located on the ten (10) position instead of the twelve (12) position, experiments have shown that (R)-10-HSA has comparable performance to R-12-HSA.

Figure 1:
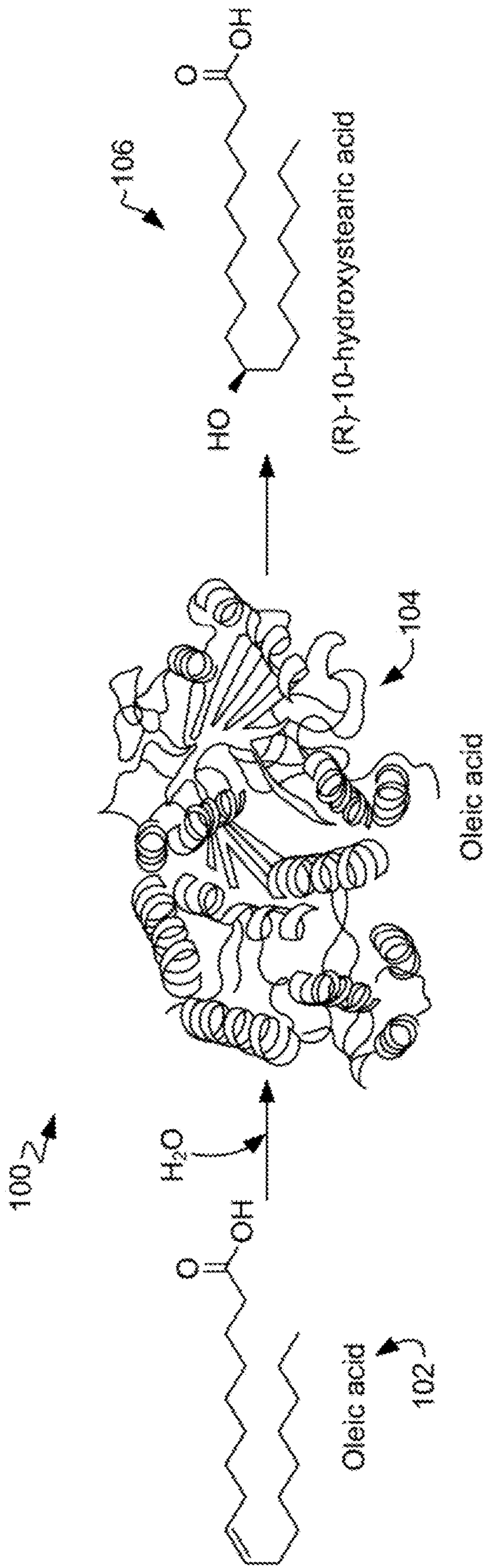
FIG. 1 is a depiction of biocatalytic conversion of oleic acid to (R)-10-hydroxystearic acid via an example oleic acid hydratase.

In various aspects, processes, methods, and compositions are provided for producing non-racemic thickening agents. In particular aspects, the thickening agent includes (R)-10-hydroxsteric acid ("(R)-10-HSA"). The processes and methods include biocatalysis using one or more recombinant oleic acid hydratase mutants. A generalized example of a biocatalysis process 100 is depicted in FIG. 1. As depicted, a molecule of oleic acid 102 reacts with water (H2O) via a catalyzed reaction mediated by oleic acid hydratase 104. The resultant product of the biocatalyzed reaction is (R)-10-HSA 106.

As discussed below, a recombinant oleic acid hydratase mutant is expressed in a bacteria that includes one or more recombinant plasmids. The recombinant oleic acid hydratase mutant is mixed with oleic acid. Non-racemic (R)-10-HSA can be extracted from the reaction media using an organic solvent. The non-racemic (R)-10-HSA can be mixed with lithium or any other metal (e.g., alkali metal, alkaline earth metals, transition metals, metalloids, or post-transition metals) to produce a non-racemic thickening agent that includes R-10-HSA. In at least one aspect, the non-racemic (R)-10-HSA is mixed with lithium (Li) to produce Li(R)-10-HSA.

Definitions

In order to clarify various terms used herein, the following definitions are provided. The following terms are used in accordance with the provided definitions throughout the description unless explicitly specified. Terms that are not specifically defined are used consistent with the common meaning within the field.

As used herein the term racemic is defined as having substantially equal amounts of left-handed and right-handed enantiomers of a chiral chemical composition.

As used herein the term non-racemic is defined as having 70% or greater enantiomeric excess.

Synthesis of Recombinant Oleic Acid Hydratase Mutants

To synthesize the recombinant oleic acid hydratase mutants described herein a wild type oleic acid hydrate from bacterial strain *Paracoccus aminophilus* (GenBank Accession No. WP_020951013) was initially selected as the parental enzyme. The enzyme was chosen as a parental enzyme based on its relative initial performance of bioconversion of oleic acid to R-10-HSA. Sun, Q. F., Y. C. Zheng, Q. Chen, J. H. Xu, and J. Pan. 2021. 'Engineering of an oleic hydratase for efficient C10-Functionalization of oleic acid', *Biochem Biophys Res Commun,* 537:64-70. The full reference DNA and amino acid sequences were identified and are included herein as SEQ ID NO: 18 and SEQ ID NO: 36, respectively.

The amino acid sequence of SEQ ID NO: 36 was provided as input data for an artificial intelligence-guided enzyme analysis. The output of the artificial intelligence system was analyzed and twelve (12) amino acid positions (Table 1) and substitution mutations were identified as having a high probability of modifying catalytic efficiency.

TABLE 1

| Amino Acid Position | Mutation |
|---|---|
| 30 | V30P |
| 41 | H41R |
| 113 | F113W |
| 153 | S153A |
| 230 | T230M |
| 245 | C245A |
| 291 | S291T |

TABLE 1-continued

| Amino Acid Position | Mutation |
|---|---|
| 336 | M336L |
| 394 | T394K |
| 432 | L432P |
| 501 | S501A |
| 508 | K508A |

Based on the output of the artificial intelligence system a library of mutated enzymes was prepared such that each enzyme variant in the library had a randomized combination of the substitutions identified in Table 1. For example, the DNA of SEQ ID NO: 18 may be mutated via Kunkel's targeted mutagenesis, Cassette mutagenesis, PCR site-directed mutagenesis, whole plasmid mutagenesis, CRISPR mediated mutagenesis, or any combination thereof. The mutated DNA was inserted into the plasmid. In some preferred aspects, the plasmid includes a promoter region (e.g., T7 promoter, lac operon, or any other suitable promoter). In some aspects described herein, the recombinant plasmids were transformed into competent bacterial cells (e.g. electrocompetent or chemically competent strains of *E. coli, Kluyveromyces lactis, Burkholderia glumae* or any other suitable bacteria).

Quality control analysis of the library was performed indicating that: 94.44% of the produced variants included a combination of the desired mutations at the 12 loci; 5.56% included insertions, deletions, or a combination thereof; and, 2.78% of the produced variants included a combination of the desired mutations at the 12 loci and included a mutation at a non-targeted location.

Evaluation of Recombinant Oleic Acid Hydratase Mutants

The library of transformed bacteria was grown in liquid growth media and screened to confirm expression of mutant oleic acid hydratase. For example, an aliquot of a particular bacterial colony in the liquid growth media was used to create 5 mL of a $10^{-6}$ dilution of the aliquot. 180 μL of the dilution was spiral plated onto an Agar plate containing Ampicillin. The plate was incubated overnight at 37° C.

After the overnight incubation, colonies from the plate were picked and added to individual wells of a first 48-well plate containing 500 μL of LB-Ampicillin per well. The 48-well plate was incubated overnight at 37° C. with mild shaking. After the overnight incubation, 20 μL of each well were added to 600 μL of LB-Ampicillin in the corresponding well of a second 48-well plate. Glycerol was added to each well of the first 48-well plate and stored at −80° C.

The second 48-well plate was incubated for three (3) hours at 37° C. and shaken at 200 rpm. The second 48-well plate was then allowed to cool to 16° C. 30 μL of 100 mM isopropyl-beta-D-thiogalactopyranoside (IPTG) was added to each well of the second 48-well plate and incubated overnight at 16° C. while being shaken at 200 rpm.

After the overnight incubation, the second plate was centrifuged at 4° C. for 10 minutes at maximum speed to pellet the cells of each well. 560 μL was decanted from each well of the second plate and 200 μL of a 10× concentrated tris-buffer-based mixture of non-ionic and zwitterionic detergents (e.g., BugBuster®) was added to each well. The cell pellets were then broken up by shaking the second 48-well plate at 500 rpm for one (1) minute. The second 48-well plate was then incubated at room temperature (e.g., approximately 20° C.) with shaking at 200 rpm.

500 μL of a substrate were added to each well of the second 48-well plate. The substrate included 200 mL 100 mM Potassium Phosphate buffer with a pH of 6.5, 500 μL Oleic Acid, and 200 μL of a surfactant (e.g., polysorbate-80). To prepare the substrate the reagents were mixed and sonicated for 15 minutes on ice.

The second 48-well plate, including the 500 μL of substrate, was incubated for 30 minutes at 30° C. while being shaken at 200 rpm. The second 48-well plate was then incubated for 15 minutes at 65° C. to deactivate the mutant oleic acid hydratase.

A colorimetric WST-8 assay was performed on each well of the 48-well plate. Each of the reagents of WST-8 master mix was prepared using a 100 mM Potassium Phosphate buffer at pH 7.5. For example, 70 mg NAD was added to 5 mL of buffer, 50 mg ADH010 was added to 2.5 mL of buffer, 30 mg WST-8 was added to 2.5 mL Buffer, 8.16 mg PMS was added to 10 mL buffer. Each individual reagent mix was kept on ice. Immediately prior to assessment, each reagent was mixed (all NAD, all ADH, all WST-8, and 250 μL PMS) together in 89.75 mL of buffer to form a WST-8 assay master mix.

The WST-8 assay was performed by duplicative plating of 20 μL of each well of the second 48-well plate to a 96-well plate. 180 μL of the WST-8 assay master mix was added to each well of the 96-well plate and incubated at room temperature for 5 minutes with gentle shaking. The absorbance of each well was determined at 450 nm.

Approximately 800 mutants were screened in a similar manner. Additionally, three (3) bacterial colonies were prepared with control plasmids. The three controls were an empty plasmid (i.e., the plasmid without a mutant oleic acid hydratase inserted), a wild type plasmid (i.e., the plasmid with SEQ. ID. 18 inserted), and a triple mutant plasmid (i.e., the plasmid with the oleic acid hydratase mutant described in Sun, Q. F., Y. C. Zheng, Q. Chen, J. H. Xu, and J. Pan. 2021. 'Engineering of an oleic hydratase for efficient C10-Functionalization of oleic acid', Biochem Biophys Res Commun, 537:64-70).

Figure 2:
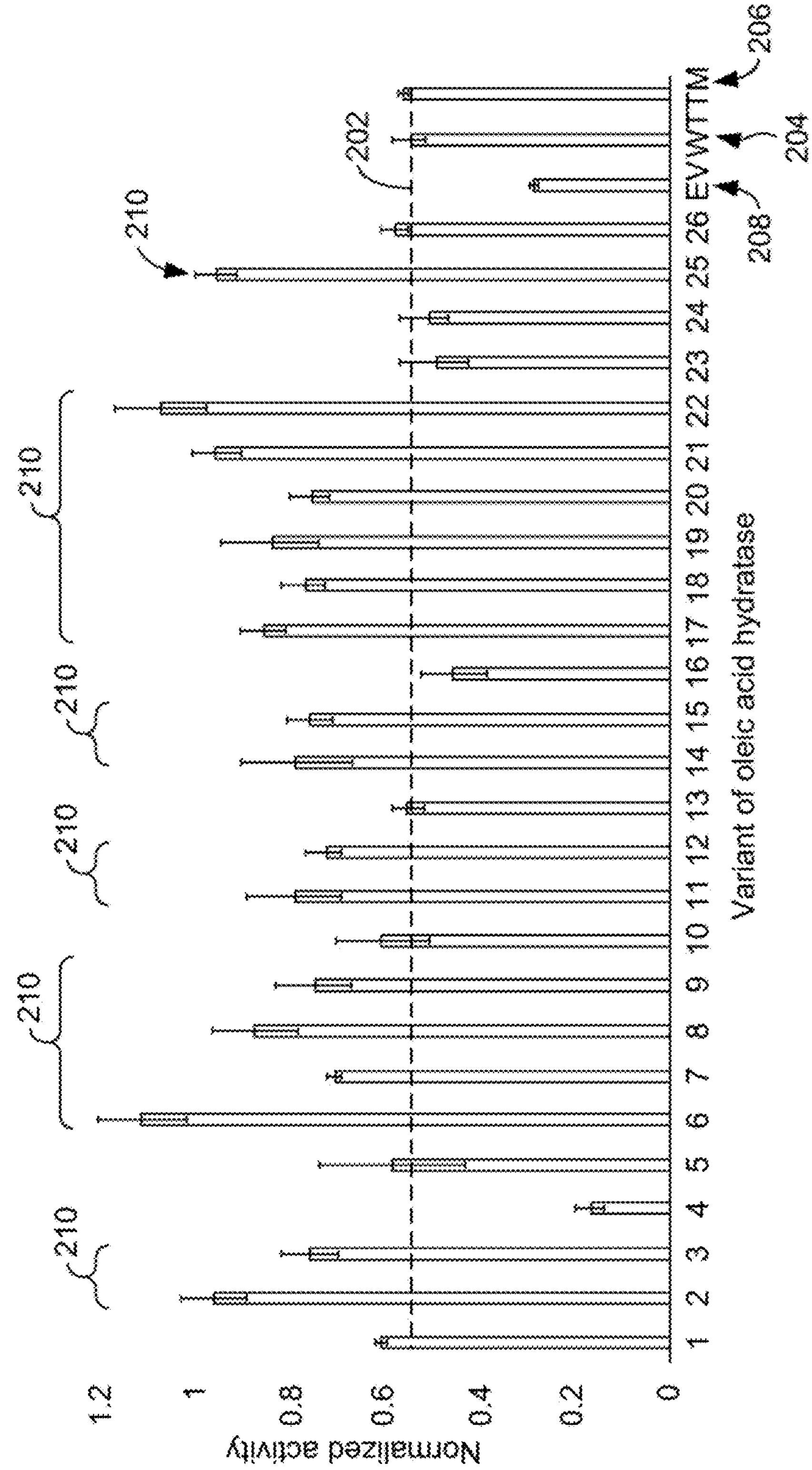
FIG. 2 is a normalized activity graph depicting selected examples of mutant oleic acid hydratase, in accordance with aspects described herein.

FIG. 2 depicts a bar graph 200 of the results of a colorimetric assay, such as described above, for a selected example portion of the mutant oleic acid hydratase normalized to the wild type parental oleic acid hydratase 204. As depicted, the dotted horizontal line 202 represents the normal wild type (WT) parental oleic acid hydratase activity 204 as detected by the colorimetric assay. As depicted, the triple mutant enzyme (TM) 206 (i.e., the enzyme produced by the bacteria containing a recombinant plasmid including the triple mutant control) had similar activity as the WT, the empty plasmid (i.e., empty vector or EV) 208 had comparatively minimal activity to the WT. Further, and advantageously, the recombinant oleic acid hydratase mutants 210 described herein demonstrated comparatively more reaction activity than the WT enzyme 204 and TM enzyme 206 in the WST-8 colorimetric assay.

Enzymes that demonstrated comparatively high reaction activity were identified and selected for larger scale bioconversion testing. For example, and turning with general reference to FIG. 3, induced cell cultures were concentrated 10-fold with potassium phosphate buffer at pH 6.5 and passed through Ultra-High Pressure Homogenizer at 28,000 PSI to break the bacterial cells and release recombinant expressed enzyme variants. The 10 mL of crude enzyme (e.g., not isolated from the cellular debris) was mixed with 10 mL emulsified oleic acid with a stir bar at 350 rpm in a small flask, at 30° C. The emulsified oleic acid can be a sonicated emulsion comprising potassium phosphate buffer at pH 6.5, 0.1% of a surfactant (e.g., polysorbat-80), and 10% oleic acid. Samples from different time points were taken, extracted with an organic solvent (e.g., ethyl acetate), and the concentrations of the substrate and product were analyzed with liquid chromatography mass spectrometry (LC-MS). The percentage of conversion was calculated with select results comparatively depicted in FIG. 3.

Figure 3A:
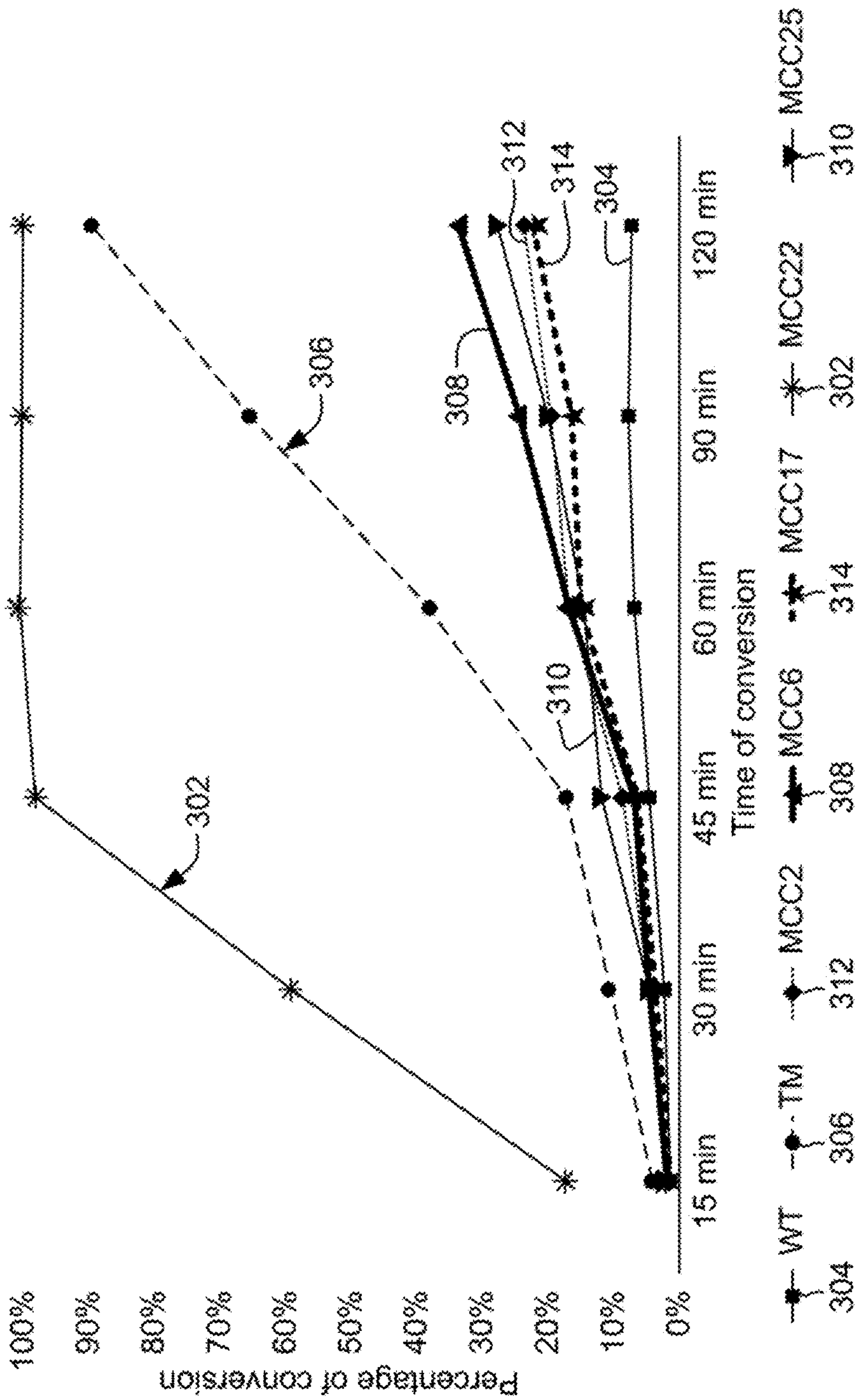
FIGS. 3A and 3B are graphs depicting conversion rates of oleic acid to (R)-10-hydroxystearic acid by selected examples of mutant oleic acid hydratase, in accordance with aspects described herein.

With specific reference to FIG. 3A, conversion rates for five of the tested enzymes are depicted in graph 300. Additionally, the conversion rates of a WT enzyme 304 and the TM enzyme 306 are depicted in graph 300. The tested enzymes depicted in graph 300 were conducted with 50% cell lysate and 50% oleic acid emulsion mixture. As depicted, the conversion rates for all tested enzymes are substantially linear within the initial 45 minutes of conversion. The performance of enzyme 302 (i.e., SEQ ID NO: 34) was unexpected with the highest percentage of conversion at ~97.4%. In comparison, within the same time frame, WT enzyme 304 only had ~5% conversion; and the best-previously known engineered enzyme (i.e., TM enzyme 306) only had ~17.1% conversion. Said differently, within the initial 45 minutes the percentage of conversion of MCC22 variant is approximately 20-fold and 6-fold of that by WT enzyme 304 and TM enzyme 306, respectively. All other selected variants described herein also show better performance than the WT enzyme 304.

Figure 3B:
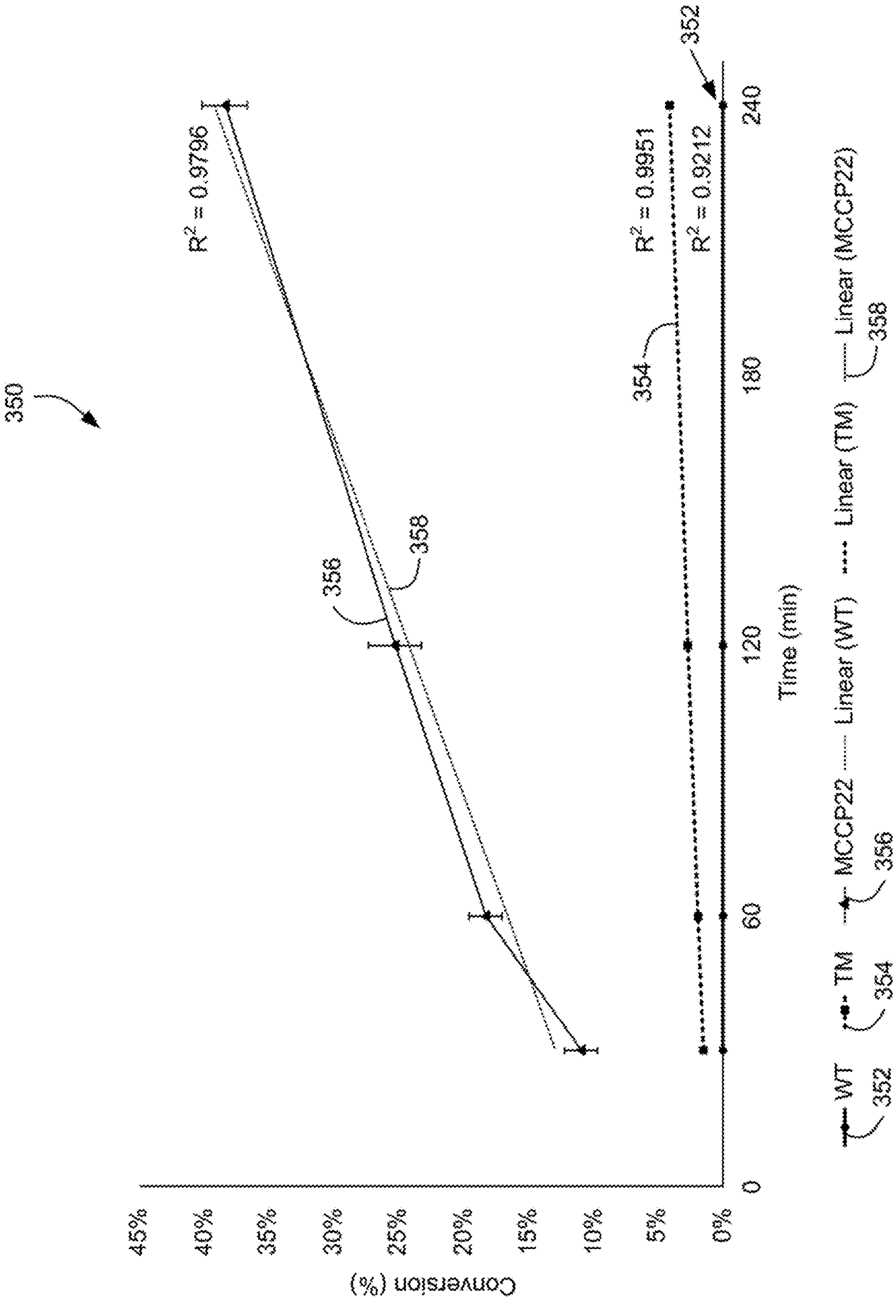

To confirm the unanticipated outstanding performance of the recombinant enzymes described herein additional testing was performed. This additional testing included, amongst other things, a reduced enzyme load rate test. Selected results of the reduced enzyme load rate test are depicted in chart 350 of FIG. 3B. The reduced enzyme load rate test conducted with 27.5% cell lysate and 72.5% of oleic acid emulsion mixture. As depicted in FIG. 3B, the conversion rate of a selected sample of the recombinant enzymes described herein (e.g., MCC22P 356) is comparatively higher than both the WT enzyme 352 and the TM enzyme 354. Said differently, the slope of the line representative of the selected recombinant enzyme depicted in FIG. 3B is steeper than both the WT enzyme and the TM enzyme. Additionally depicted in FIG. 3B is the linearized rate for each of the included enzymes (e.g., Linear (MCC22P) 358).

Sequencing and Quantification of Recombinant Oleic Acid Hydratase Mutants

Traditional techniques for amino acid (AA) sequencing and deoxyribonucleic acid (DNA) sequencing were used to determine the sequence for all tested mutants. For example, the DNA sequence of SEQ. ID. Nos. 1-17 were confirmed using Sanger sequencing or Next-Generation sequencing (NGS). Similarly, the AA sequence of SEQ. ID. Nos. 19-35 were confirmed using mass spectrometry or Edman degradation. Additionally, the AA and DNA sequences for the WT enzyme and TM enzyme were determined using the same traditional techniques. The DNA sequence of each of the mutant oleic acid hydratases (i.e., SEQ. ID. Nos. 1-17) are provided in Table 2 below. The AA sequence of each of the mutant oleic acid hydratases (i.e., SEQ. ID. Nos. 19-35) are provided in Table 3 below.

TABLE 2

| SEQ ID NO: Ref | Ref Name | Amino Acid Sequence |
|---|---|---|
| SEQ ID NO: 1 | MCC2 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCGCCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC<br>TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTACCGTGACCGGCATTCTCGCCAGCGTTAACGGTCAAGAACATC<br>GTATCCCGGTAGATGAAAAAGATGTGGTGTTCGCTCTGACTGGCA<br>GCATGACGGAGGGAACGGCCTACGGTGATATGGACCACGCACCAG<br>TTCTGGAACGTGGACGTTCTGACCCGGGTCCGGACTCGGACTGGGC<br>ATTATGGCAGAACCTTGCGGCTAAGAGCCCGATCTTTGGCAACCCG<br>AAAAAGTTTTACGGCGACATCGATAAATCCATGTGGGAAAGCGGT<br>ACACTGACGTGCAAACCGAGCCCACTGACCGATCGTCTGACGGAG<br>CTTTCCGTGAACGACCCGTACAGCGGTAAGACCGTGACCGGCGGT<br>ATCATCACCTTTACCGATAGTAACTGGGTGATGAGCGTGACCTGCA<br>ACCGTCAGCCGCATTTTCCGGGCCAACCGAAGGATGTTCTGGTCTT<br>GTGGGTCTATGCACTGCTTATGGACAAAGACGGAAACAAAGTGAA<br>GAAGCCGATGCCGGCATGTACCGGCCGCGAAATATTGGCGGAATT<br>GTGTCACCACCTAGGCATCCCGGACGACCAGTTCGAAGCTGTGGCT<br>GCGAAGACCAAAGTTCGTCTCGCTCTGATGCCGTATATTACCAGCA<br>TGTTCATGCCGCGTGCGAAGGGTGACCGTCCGCACGTTGTTCCGGA<br>GGGCTGCACTAATCTGGCGCTGATGGGTCAGTTCGTTGAGACGGCC<br>AATGACATCGTGTTCACCATGGATTCTAGCATTCGTACCGCGCGTA<br>TTGGTGTTTATACCCTGTTGGGCCTGCGTAAGCAGGTTCCGGACAT<br>CAGCCCGGTCCAGTATGATATCCGCACGCTGATTAAAGCCGCGCG<br>CACGGTTAACAACAACCAGCCGTTTCCGGGCGAGAGGCTGTTACA<br>CCGTCTGCTTGGTAAAACGTATTACGCCCATATTCTGCCTCCGCTG<br>CCAGATCGCACCCAGACCACCCGCGACGCGGCTGAAACCGAATTG<br>AAGGCCTTCCTCGGCACCGGTGGCACTGCGTTAGCAGCGGTTGGTG<br>GTTGGCTGCAGCGTGTACGTGAGGATCTGAAAGAGCGCACCCGTA<br>AG |
| SEQ. ID. No. 2 | MCC3 | ATGAGTCCCAAGACATCAAAACCATTTCACGTGGAGAACGACACC<br>ACCGCGGGTTATTGGTCCAACCGTCCGGAAAATACCCTGCCACCGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGGCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACACCCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTAGCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTATGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGACGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG |

TABLE 2-continued

| SEQ ID NO: Ref | Ref Name | Amino Acid Sequence |
|---|---|---|
| | | AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCGC<br>CATGTTCATGCCGCGTGCGAAGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 3 | MCC6 | ATGAGTCCCAAGACATCAAAACCATTTCACGTGGAGAACGACACC<br>ACCGCGGGTTATTGGTCCAACCGTCCGGAAAATACCCTGCCACCGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC<br>TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTACCGTGACCGGCATTCTCGCCAGCGTTAACGGTCAAGAACATC<br>GTATCCCGGTAGATGAAAAAGATGTGGTGTTCGCTCTGACTGGCA<br>GCATGACGGAGGGAACGGCCTACGGTGATATGGACCACGCACCAG<br>TTCTGGAACGTGGACGTTCTGACCCGGGTCCGGACTCGGACTGGGC<br>ATTATGGCAGAACCTTGCGGCTAAGAGCCCGATCTTTGGCAACCCG<br>AAAAAGTTTTACGGCGACATCGATAAATCCATGTGGGAAAGCGGT<br>ACACTGACGTGCAAACCGAGCCCACTGACCGATCGTCTGACGGAG<br>CTTTCCGTGAACGACCCGTACAGCGGTAAGACCGTGACCGGCGGT<br>ATCATCACCTTTACCGATAGTAACTGGGTGATGAGCGTGACCTGCA<br>ACCGTCAGCCGCATTTTCCGGGCCAACCGAAGGATGTTCTGGTCTT<br>GTGGGTCTATGCACTGCTTATGGACAAAGACGGAAACAAAGTGAA<br>GAAGCCGATGCCGGCATGTACCGGCCGCGAAATATTGGCGGAATT<br>GTGTCACCACCTAGGCATCCCGGACGACCAGTTCGAAGCTGTGGCT<br>GCGAAGACCAAAGTTCGTCTCGCTCTGATGCCGTATATTACCAGCA<br>TGTTCATGCCGCGTGCGAAGGGTGACCGTCCGCACGTTGTTCCGGA<br>GGGCTGCACTAATCTGGCGCTGATGGGTCAGTTCGTTGAGACGGCC<br>AATGACATCGTGTTCACCATGGATTCTAGCATTCGTACCGCGCGTA<br>TTGGTGTTTATACCCTGTTGGGCCTGCGTAAGCAGGTTCCGGACAT<br>CAGCCCGGTCCAGTATGATATCCGCACGCTGATTAAAGCCGCGCG<br>CACGGTTAACAACAACCAGCCGTTTCCGGGCGAGAGGCTGTTACA<br>CCGTCTGCTTGGTAAAACGTATTACGCCCATATTCTGCCTCCGCTG<br>CCAGATCGCACCCAGACCACCCGCGACGCGGCTGAAACCGAATTG<br>AAGGCCTTCCTCGGCACCGGTGGCACTGCGTTAGCAGCGGTTGGTG<br>GTTGGCTGCAGCGTGTACGTGAGGATCTGAAAGAGCGCACCCGTA<br>AG |
| SEQ ID NO: 4 | MCC7 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGTCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT |

TABLE 2-continued

| SEQ ID NO: Ref | Ref Name | Amino Acid Sequence |
|---|---|---|
| | | CTACACCCATCGCTTTCTGGATTCTATCGACGGTTTCGCGGATATG TCCTGCCTGGTTTTCCCGAAGTATAATCAGCATGATACCTTCGTTA AACCTCTGGTGGATCATCTCAAGAAGCTGGGGGTGCAAGTTCAATT TGCGACCCGTGTTAGCGACCTGGAGATGACTGAAGATGCAGGCAA ACGTACCGTGACCGGCATTCTCGCCAGCGTTAACGGTCAAGAACA TCGTATCCCGGTAGATGAAAAAGATGTGGTGTTCGCTCTGACTGGC AGCATGACGGAGGGAACGGCCTACGGTGATATGGACCACGCACCA GTTCTGGAACGTGGACGTTCTGACCCGGGTCCGGACTCGGACTGG GCATTATGGCAGAACCTTGCGGCTAAGAGCCCGATCTTTGGCAACC CGAAAAAGTTTTACGGCGACATCGATAAATCCATGTGGGAAAGCG GTACACTGACGTGCAAACCGAGCCCACTGACCGATCGTCTGACGG AGCTTTCCGTGAACGACCCGTACAGCGGTAAGACCGTGACCGGCG GTATCATCACCTTTACCGATAGTAACTGGGTGATGAGCGTGACCTG CAACCGTCAGCCGCATTTTCCGGGCCAACCGAAGGATGTTCTGGTC TTGTGGGTCTATGCACTGCTTATGGACAAAGACGGAAACAAAGTG AAGAAGCCGATGCCGGCATGTACCGGCCGCGAAATATTGGCGGAA TTGTGTCACCACCTAGGCATCCCGGACGACCAGTTCGAAGCTGTGG CTGCGAAGACCAAAGTTCGTCTCGCTCTGATGCCGTATATTACCAG CATGTTCATGCCGCGTGCGGCGGGTGACCGTCCGCACGTTGTTCCG GAGGGCTGCACTAATCTGGCGCTGATGGGTCAGTTCGTTGAGACG GCCAATGACATCGTGTTCACCATGGATTCTAGCATTCGTACCGCGC GTATTGGTGTTTATACCCTGTTGGGCCTGCGTAAGCAGGTTCCGGA CATCAGCCCGGTCCAGTATGATATCCGCACGCTGATTAAAGCCGCG CGCACGGTTAACAACAACCAGCCGTTTCCGGGCGAGAGGCTGTTA CACCGTCTGCTTGGTAAAACGTATTACGCCCATATTCTGCCTCCGC TGCCAGATCGCACCCAGACCACCCGCGACGCGGCTGAAACCGAAT TGAAGGCCTTCCTCGGCACCGGTGGCACTGCGTTAGCAGCGGTTGG TGGTTGGCTGCAGCGTGTACGTGAGGATCTGAAAGAGCGCACCCG TAAG |
| SEQ ID NO: 5 | MCC8 | ATGAGTCCCAAGACATCAAAACCATTTCACGTGGAGAACGACACC ACCGCGGGTTATTGGTCCAACCGTCCGGAAAATACCCTGCCACCGC CGGACATGATGGGTGCGTACATGCGTAATCGCCCGTACCCGGGCA ACCAAGTCGAGGGCCGCAAGGCATGGATTATCGGCTCTGGTATTG CAGGCCTGGCGGCGGCGTTTTACCTGATTCGCGATGGTGGCATGAA AGGTCAAGACATCACCATTTTAGATGCATTGGACGTCACTGGCGGT TCCCTGGACGGCGCGGGTAATCCGGAAGACGGGTACATCATTCGT GGTGGTCGGGAGATGAACTTCAATTATGACAACTTGTGGGATATGT TTCAAGATGTGCAAGCGCTGGAGCTCCCGGAGGGCTACTCGGTTCT GGACGAGTATCGCCAACTGAATGACGCTGATCCGAATTGGAGCAA GGCCCGTCTGATGCACAATCAGGGTGAGATCAGAGATTTCAGCAC CTTTGGTCTGACGAAACCGCAGCAGTGGGAACTCATCAGATTGTTG TTGAAGCGCAAAGAAGACCTGGACGATCTGACCATTGAAGATTAC TTTTCGCCGGGTTTCTTACAAAGCAACTTTTGGTTTCTGTGGCGTTC TATGTTCGCCTTCGAGAACTGGCAGAGCCTGTTGGAGATGAAACTC TACACCCATCGCTTTCTGGATTCTATCGACGGTTTCGCGGATATGT CCTGCCTGGTTTTCCCGAAGTATAATCAGCATGATACCTTCGTTAA ACCTCTGGTGGATCATCTCAAGAAGCTGGGGGTGCAAGTTCAATTT GCGACCCGTGTTAGCGACCTGGAGATGACTGAAGATGCAGGCAAA CGTAGCGTGACCGGCATTCTCGCCAGCGTTAACGGTCAAGAACAT CGTATCCCGGTAGATGAAAAAGATGTGGTGTTCGCTCTGACTGGCA GCATGACGGAGGGAACGGCCTACGGTGATATGGACCACGCACCAG TTCTGGAACGTGGACGTTCTGACCCGGGTCCGGACTCGGACTGGGC ATTATGGCAGAACCTTGCGGCTAAGAGCCCGATCTTTGGCAACCCG AAAAAGTTTTACGGCGACATCGATAAATCCATGTGGGAAAGCGGT ACACTGACGTGCAAACCGAGCCCACTGACCGATCGTCTGAAGGAG CTTTCCGTGAACGACCCGTACAGCGGTAAGACCGTGACCGGCGGT ATCATCACCTTTACCGATAGTAACTGGGTGATGAGCGTGACCTGCA ACCGTCAGCCGCATTTTCCGGGCCAACCGAAGGATGTTCTGGTCTT GTGGGTCTATGCACTGCTTATGGACAAAGACGGAAACAAAGTGAA GAAGCCGATGCCGGCATGTACCGGCCGCGAAATATTGGCGGAATT GTGTCACCACCTAGGCATCCCGGACGACCAGTTCGAAGCTGTGGCT GCGAAGACCAAAGTTCGTCTCGCTCTGATGCCGTATATTACCGCCA TGTTCATGCCGCGTGCGAAGGGTGACCGTCCGCACGTTGTTCCGGA GGGCTGCACTAATCTGGCGCTGATGGGTCAGTTCGTTGAGACGGCC AATGACATCGTGTTCACCATGGATTCTAGCATTCGTACCGCGCGTA TTGGTGTTTATACCCTGTTGGGCCTGCGTAAGCAGGTTCCGGACAT CAGCCCGGTCCAGTATGATATCCGCACGCTGATTAAAGCCGCGCG CACGGTTAACAACAACCAGCCGTTTCCGGGCGAGAGGCTGTTACA CCGTCTGCTTGGTAAAACGTATTACGCCCATATTCTGCCTCCGCTG CCAGATCGCACCCAGACCACCCGCGACGCGGCTGAAACCGAATTG AAGGCCTTCCTCGGCACCGGTGGCACTGCGTTAGCAGCGGTTGGTG GTTGGCTGCAGCGTGTACGTGAGGATCTGAAAGAGCGCACCCGTA AG |

TABLE 2-continued

| SEQ ID NO: Ref | Ref Name | Amino Acid Sequence |
|---|---|---|
| SEQ ID NO: 6 | MCC9 | ATGAGTCCCAAGACATCAAAACCATTTCACGTGGAGAACGACACC<br>ACCGCGGGTTATTGGTCCAACCGTCCGGAAAATACCCTGCCACCGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGTCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACACCCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTAGCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTATGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGAAGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG<br>AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGGCGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 7 | MCC11 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCGCCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGTCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACACCCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTAGCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTCTGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGAAGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG |

TABLE 2-continued

| SEQ ID NO: Ref | Ref Name | Amino Acid Sequence |
|---|---|---|
| | | AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGGCGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 8 | MCC12 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGGCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACATGCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTACCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTATGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGAAGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG<br>AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGGCGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 9 | MCC14 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC |

TABLE 2-continued

| SEQ ID NO: Ref | Ref Name | Amino Acid Sequence |
|---|---|---|
| | | TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTAGCGTGACCGGCATTCTCGCCAGCGTTAACGGTCAAGAACAT<br>CGTATCCCGGTAGATGAAAAAGATGTGGTGTTCGCTCTGACTGGCA<br>GCATGACGGAGGGAACGGCCTACGGTGATATGGACCACGCACCAG<br>TTATGGAACGTGGACGTTCTGACCCGGGTCCGGACTCGGACTGGG<br>CATTATGGCAGAACCTTGCGGCTAAGAGCCCGATCTTTGGCAACCC<br>GAAAAAGTTTTACGGCGACATCGATAAATCCATGTGGGAAAGCGG<br>TACACTGACGTGCAAACCGAGCCCACTGACCGATCGTCTGAAGGA<br>GCTTTCCGTGAACGACCCGTACAGCGGTAAGACCGTGACCGGCGG<br>TATCATCACCTTTACCGATAGTAACTGGGTGATGAGCGTGACCTGC<br>AACCGTCAGCCGCATTTTCTGGGCCAACCGAAGGATGTTCTGGTCT<br>TGTGGGTCTATGCACTGCTTATGGACAAAGACGGAAACAAAGTGA<br>AGAAGCCGATGCCGGCATGTACCGGCCGCGAAATATTGGCGGAAT<br>TGTGTCACCACCTAGGCATCCCGGACGACCAGTTCGAAGCTGTGGC<br>TGCGAAGACCAAAGTTCGTCTCGCTCTGATGCCGTATATTACCAGC<br>ATGTTCATGCCGCGTGCGAAGGGTGACCGTCCGCACGTTGTTCCGG<br>AGGGCTGCACTAATCTGGCGCTGATGGGTCAGTTCGTTGAGACGG<br>CCAATGACATCGTGTTCACCATGGATTCTAGCATTCGTACCGCGCG<br>TATTGGTGTTTATACCCTGTTGGGCCTGCGTAAGCAGGTTCCGGAC<br>ATCAGCCCGGTCCAGTATGATATCCGCACGCTGATTAAAGCCGCGC<br>GCACGGTTAACAACAACCAGCCGTTTCCGGGCGAGAGGCTGTTAC<br>ACCGTCTGCTTGGTAAAACGTATTACGCCCATATTCTGCCTCCGCT<br>GCCAGATCGCACCCAGACCACCCGCGACGCGGCTGAAACCGAATT<br>GAAGGCCTTCCTCGGCACCGGTGGCACTGCGTTAGCAGCGGTTGGT<br>GGTTGGCTGCAGCGTGTACGTGAGGATCTGAAAGAGCGCACCCGT<br>AAG |
| SEQ ID NO: 10 | MCC15 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGTCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACATGCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTAGCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTCTGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGACGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG<br>AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGAAGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |

TABLE 2-continued

| SEQ ID NO: Ref | Ref Name | Amino Acid Sequence |
|---|---|---|
| SEQ ID NO: 11 | MCC17 | ATGAGTCCCAAGACATCAAAACCATTTCACGTGGAGAACGACACC<br>ACCGCGGGTTATTGGTCCAACCGTCCGGAAAATACCCTGCCAGTG<br>CCGGACATGATGGGTGCGTACATGCGTAATCACCCGTACCCGGGC<br>AACCAAGTCGAGGGCCGCAAGGCATGGATTATCGGCTCTGGTATT<br>GCAGGCCTGGCGGCGGCGTTTTACCTGATTCGCGATGGTGGCATG<br>AAAGGTCAAGACATCACCATTTTAGATGCATTGGACGTCACTGGC<br>GGTTCCCTGGACGGCGCGGGTAATCCGGAAGACGGGTACATCATT<br>CGTGGTGGTCGGGAGATGAACTTCAATTATGACAACTTGTGGGAT<br>ATGTTTCAAGATGTGCAAGCGCTGGAGCTCCCGGAGGGCTACTCG<br>GTTCTGGACGAGTATCGCCAACTGAATGACGCTGATCCGAATTGG<br>AGCAAGTCCCGTCTGATGCACAATCAGGGTGAGATCAGAGATTTC<br>AGCACCTTTGGTCTGACGAAACCGCAGCAGTGGGAACTCATCAGA<br>TTGTTGTTGAAGCGCAAAGAAGACCTGGACGATCTGACCATTGAA<br>GATTACTTTTCGCCGGGTTTCTTACAAAGCAACTTTTGGTTTCTGTG<br>GCGTTCTATGTTCGCCTTCGAGAACTGGCAGAGCCTGTTGGAGATG<br>AAACTCTACACCCATCGCTTTCTGGATTCTATCGACGGTTTCGCGG<br>ATATGTCCTGCCTGGTTTTCCCGAAGTATAATCAGCATGATACCTT<br>CGTTAAACCTCTGGTGGATCATCTCAAGAAGCTGGGGGTGCAAGT<br>TCAATTTGCGACCCGTGTTAGCGACCTGGAGATGACTGAAGATGC<br>AGGCAAACGTAGCGTGACCGGCATTCTCGCCAGCGTTAACGGTCA<br>AGAACATCGTATCCCGGTAGATGAAAAAGATGTGGTGTTCGCTCT<br>GACTGGCAGCATGACGGAGGGAACGGCCTACGGTGATATGGACCA<br>CGCACCAGTTATGGAACGTGGACGTTCTGACCCGGGTCCGGACTC<br>GGACTGGGCATTATGGCAGAACCTTGCGGCTAAGAGCCCGATCTT<br>TGGCAACCCGAAAAAGTTTTACGGCGACATCGATAAATCCATGTG<br>GGAAAGCGGTACACTGACGTGCAAACCGAGCCCACTGACCGATCG<br>TCTGAAGGAGCTTTCCGTGAACGACCCGTACAGCGGTAAGACCGT<br>GACCGGCGGTATCATCACCTTTACCGATAGTAACTGGGTGATGAG<br>CGTGACCTGCAACCGTCAGCCGCATTTTCCGGGCCAACCGAAGGA<br>TGTTCTGGTCTTGTGGGTCTATGCACTGCTTATGGACAAAGACGGA<br>AACAAAGTGAAGAAGCCGATGCCGGCATGTACCGGCCGCGAAAT<br>ATTGGCGGAATTGTGTCACCACCTAGGCATCCCGGACGACCAGTT<br>CGAAGCTGTGGCTGCGAAGACCAAAGTTCGTCTCGCTCTGATGCC<br>GTATATTACCAGCATGTTCATGCCGCGTGCGGCGGGTGACCGTCCG<br>CACGTTGTTCCGGAGGGCTGCACTAATCTGGCGCTGATGGGTCAGT<br>TCGTTGAGACGGCCAATGACATCGTGTTCACCATGGATTCTAGCAT<br>TCGTACCGCGCGTATTGGTGTTTATACCCTGTTGGGCCTGCGTAAG<br>CAGGTTCCGGACATCAGCCCGGTCCAGTATGATATCCGCACGCTG<br>ATTAAAGCCGCGCGCACGGTTAACAACAACCAGCCGTTTCCGGGC<br>GAGAGGCTGTTACACCGTCTGCTTGGTAAAACGTATTACGCCCATA<br>TTCTGCCTCCGCTGCCAGATCGCACCCAGACCACCCGCGACGCGG<br>CTGAAACCGAATTGAAGGCCTTCCTCGGCACCGGTGGCACTGCGT<br>TAGCAGCGGTTGGTGGTTGGCTGCAGCGTGTACGTGAGGATCTGA<br>AAGAGCGCACCCGTAAG |
| SEQ ID NO: 12 | MCC18 | ATGAGTCCCAAGACATCAAAACCATTICACGTGGAGAACGACACC<br>ACCGCGGGTTATTGGTCCAACCGTCCGGAAAATACCCTGCCAGTGC<br>CGGACATGATGGGTGCGTACATGCGTAATCGCCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGGCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACATGCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTACCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTCTGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGACGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG |

TABLE 2-continued

| SEQ ID NO: Ref | Ref Name | Amino Acid Sequence |
|---|---|---|
| | | AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGAAGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 13 | MCC19 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCGCCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTGGAATTATGACAACTTGTGGGATATG<br>TTTCAAGATGTGCAAGCGCTGGAGCTCCCGGAGGGCTACTCGGTTC<br>TGGACGAGTATCGCCAACTGAATGACGCTGATCCGAATTGGAGCA<br>AGTCCCGTCTGATGCACAATCAGGGTGAGATCAGAGATTTCAGCA<br>CCTTTGGTCTGACGAAACCGCAGCAGTGGGAACTCATCAGATTGTT<br>GTTGAAGCGCAAAGAAGACCTGGACGATCTGACCATTGAAGATTA<br>CTTTTCGCCGGGTTTCTTACAAAGCAACTTTTGGTTTCTGTGGCGTT<br>CTATGTTCGCCTTCGAGAACTGGCAGAGCCTGTTGGAGATGAAACT<br>CTACACCCATCGCTTTCTGGATTCTATCGACGGTTTCGCGGATATG<br>TCCTGCCTGGTTTTCCCGAAGTATAATCAGCATGATACCTTCGTTA<br>AACCTCTGGTGGATCATCTCAAGAAGCTGGGGGTGCAAGTTCAATT<br>TGCGACCCGTGTTAGCGACCTGGAGATGACTGAAGATGCAGGCAA<br>ACGTACCGTGACCGGCATTCTCGCCAGCGTTAACGGTCAAGAACA<br>TCGTATCCCGGTAGATGAAAAAGATGTGGTGTTCGCTCTGACTGGC<br>AGCATGACGGAGGGAACGGCCTACGGTGATATGGACCACGCACCA<br>GTTATGGAACGTGGACGTTCTGACCCGGGTCCGGACTCGGACTGG<br>GCATTATGGCAGAACCTTGCGGCTAAGAGCCCGATCTTTGGCAACC<br>CGAAAAAGTTTTACGGCGACATCGATAAATCCATGTGGGAAAGCG<br>GTACACTGACGTGCAAACCGAGCCCACTGACCGATCGTCTGAAGG<br>AGCTTTCCGTGAACGACCCGTACAGCGGTAAGACCGTGACCGGCG<br>GTATCATCACCTTTACCGATAGTAACTGGGTGATGAGCGTGACCTG<br>CAACCGTCAGCCGCATTTTCCGGGCCAACCGAAGGATGTTCTGGTC<br>TTGTGGGTCTATGCACTGCTTATGGACAAAGACGGAAACAAAGTG<br>AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGAAGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 14 | MCC20 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCGCCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC |

TABLE 2-continued

| SEQ ID NO: Ref | Ref Name | Amino Acid Sequence |
|---|---|---|
| | | TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTAGCGTGACCGGCATTCTCGCCAGCGTTAACGGTCAAGAACAT<br>CGTATCCCGGTAGATGAAAAAGATGTGGTGTTCGCTCTGACTGGCA<br>GCATGACGGAGGGAACGGCCTACGGTGATATGGACCACGCACCAG<br>TTATGGAACGTGGACGTTCTGACCCGGGTCCGGACTCGGACTGGG<br>CATTATGGCAGAACCTTGCGGCTAAGAGCCCGATCTTTGGCAACCC<br>GAAAAAGTTTTACGGCGACATCGATAAATCCATGTGGGAAAGCGG<br>TACACTGACGTGCAAACCGAGCCCACTGACCGATCGTCTGACGGA<br>GCTTTCCGTGAACGACCCGTACAGCGGTAAGACCGTGACCGGCGG<br>TATCATCACCTTTACCGATAGTAACTGGGTGATGAGCGTGACCTGC<br>AACCGTCAGCCGCATTTTCCGGGCCAACCGAAGGATGTTCTGGTCT<br>TGTGGGTCTATGCACTGCTTATGGACAAAGACGGAAACAAAGTGA<br>AGAAGCCGATGCCGGCATGTACCGGCCGCGAAATATTGGCGGAAT<br>TGTGTCACCACCTAGGCATCCCGGACGACCAGTTCGAAGCTGTGGC<br>TGCGAAGACCAAAGTTCGTCTCGCTCTGATGCCGTATATTACCAGC<br>ATGTTCATGCCGCGTGCGAAGGGTGACCGTCCGCACGTTGTTCCGG<br>AGGGCTGCACTAATCTGGCGCTGATGGGTCAGTTCGTTGAGACGG<br>CCAATGACATCGTGTTCACCATGGATTCTAGCATTCGTACCGCGCG<br>TATTGGTGTTTATACCCTGTTGGGCCTGCGTAAGCAGGTTCCGGAC<br>ATCAGCCCGGTCCAGTATGATATCCGCACGCTGATTAAAGCCGCGC<br>GCACGGTTAACAACAACCAGCCGTTTCCGGGCGAGAGGCTGTTAC<br>ACCGTCTGCTTGGTAAAACGTATTACGCCCATATTCTGCCTCCGCT<br>GCCAGATCGCACCCAGACCACCCGCGACGCGGCTGAAACCGAATT<br>GAAGGCCTTCCTCGGCACCGGTGGCACTGCGTTAGCAGCGGTTGGT<br>GGTTGGCTGCAGCGTGTACGTGAGGATCTGAAAGAGCGCACCCGT<br>AAG |
| SEQ ID NO: 15 | MCC21 | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC<br>TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTAGCGTGACCGGCATTCTCGCCAGCGTTAACGGTCAAGAACAT<br>CGTATCCCGGTAGATGAAAAAGATGTGGTGTTCGCTCTGACTGGCA<br>GCATGACGGAGGGAACGGCCTACGGTGATATGGACCACGCACCAG<br>TTCTGGAACGTGGACGTTCTGACCCGGGTCCGGACTCGGACTGGGC<br>ATTATGGCAGAACCTTGCGGCTAAGAGCCCGATCTTTGGCAACCCG<br>AAAAAGTTTTACGGCGACATCGATAAATCCATGTGGGAAAGCGGT<br>ACACTGACGTGCAAACCGAGCCCACTGACCGATCGTCTGACGGAG<br>CTTTCCGTGAACGACCCGTACAGCGGTAAGACCGTGACCGGCGGT<br>ATCATCACCTTTACCGATAGTAACTGGGTGATGAGCGTGACCTGCA<br>ACCGTCAGCCGCATTTTCCGGGCCAACCGAAGGATGTTCTGGTCTT<br>GTGGGTCTATGCACTGCTTATGGACAAAGACGGAAACAAAGTGAA<br>GAAGCCGATGCCGGCATGTACCGGCCGCGAAATATTGGCGGAATT<br>GTGTCACCACCTAGGCATCCCGGACGACCAGTTCGAAGCTGTGGCT<br>GCGAAGACCAAAGTTCGTCTCGCTCTGATGCCGTATATTACCAGCA<br>TGTTCATGCCGCGTGCGAAGGGTGACCGTCCGCACGTTGTTCCGGA<br>GGGCTGCACTAATCTGGCGCTGATGGGTCAGTTCGTTGAGACGGCC<br>AATGACATCGTGTTCACCATGGATTCTAGCATTCGTACCGCGCGTA<br>TTGGTGTTTATACCCTGTTGGGCCTGCGTAAGCAGGTTCCGGACAT<br>CAGCCCGGTCCAGTATGATATCCGCACGCTGATTAAAGCCGCGCG<br>CACGGTTAACAACAACCAGCCGTTTCCGGGCGAGAGGCTGTTACA<br>CCGTCTGCTTGGTAAAACGTATTACGCCCATATTCTGCCTCCGCTG<br>CCAGATCGCACCCAGACCACCCGCGACGCGGCTGAAACCGAATTG<br>AAGGCCTTCCTCGGCACCGGTGGCACTGCGTTAGCAGCGGTTGGTG<br>GTTGGCTGCAGCGTGTACGTGAGGATCTGAAAGAGCGCACCCGTA<br>AG |

TABLE 2-continued

| SEQ ID NO: Ref | Ref Name | Amino Acid Sequence |
|---|---|---|
| SEQ ID NO: 16 | MCC22 | ATGAGTCCCAAGACATCAAAACCATTTCACGTGGAGAACGACACC ACCGCGGGTTATTGGTCCAACCGTCCGGAAAATACCCTGCCAGTGC CGGACATGATGGGTGCGTACATGCGTAATCGCCCGTACCCGGGCA ACCAAGTCGAGGGCCGCAAGGCATGGATTATCGGCTCTGGTATTG CAGGCCTGGCGGCGGCGTTTTACCTGATTCGCGATGGTGGCATGAA AGGTCAAGACATCACCATTTTAGATGCATTGGACGTCACTGGCGGT TCCCTGGACGGCGCGGGTAATCCGGAAGACGGGTACATCATTCGT GGTGGTCGGGAGATGAACTGGAATTATGACAACTTGTGGGATATG TTTCAAGATGTGCAAGCGCTGGAGCTCCCGGAGGGCTACTCGGTTC TGGACGAGTATCGCCAACTGAATGACGCTGATCCGAATTGGAGCA AGTCCCGTCTGATGCACAATCAGGGTGAGATCAGAGATTTCAGCA CCTTTGGTCTGACGAAACCGCAGCAGTGGGAACTCATCAGATTGTT GTTGAAGCGCAAAGAAGACCTGGACGATCTGACCATTGAAGATTA CTTTTCGCCGGGTTTCTTACAAAGCAACTTTTGGTTTCTGTGGCGTT CTATGTTCGCCTTCGAGAACTGGCAGAGCCTGTTGGAGATGAAACT CTACACCCATCGCTTTCTGGATTCTATCGACGGTTTCGCGGATATG TCCTGCCTGGTTTTCCCGAAGTATAATCAGCATGATACCTTCGTTA AACCTCTGGTGGATCATCTCAAGAAGCTGGGGGTGCAAGTTCAATT TGCGACCCGTGTTAGCGACCTGGAGATGACTGAAGATGCAGGCAA ACGTAGCGTGACCGGCATTCTCGCCAGCGTTAACGGTCAAGAACA TCGTATCCCGGTAGATGAAAAAGATGTGGTGTTCGCTCTGACTGGC AGCATGACGGAGGGAACGGCCTACGGTGATATGGACCACGCACCA GTTATGGAACGTGGACGTTCTGACCCGGGTCCGGACTCGGACTGG GCATTATGGCAGAACCTTGCGGCTAAGAGCCCGATCTTTGGCAACC CGAAAAAGTTTTACGGCGACATCGATAAATCCATGTGGGAAAGCG GTACACTGACGTGCAAACCGAGCCCACTGACCGATCGTCTGACGG AGCTTTCCGTGAACGACCCGTACAGCGGTAAGACCGTGACCGGCG GTATCATCACCTTTACCGATAGTAACTGGGTGATGAGCGTGACCTG CAACCGTCAGCCGCATTTTCCGGGCCAACCGAAGGATGTTCTGGTC TTGTGGGTCTATGCACTGCTTATGGACAAAGACGGAAACAAAGTG AAGAAGCCGATGCCGGCATGTACCGGCCGCGAAATATTGGCGGAA TTGTGTCACCACCTAGGCATCCCGGACGACCAGTTCGAAGCTGTGG CTGCGAAGACCAAAGTTCGTCTCGCTCTGATGCCGTATATTACCGC CATGTTCATGCCGCGTGCGAAGGGTGACCGTCCGCACGTTGTTCCG GAGGGCTGCACTAATCTGGCGCTGATGGGTCAGTTCGTTGAGACG GCCAATGACATCGTGTTCACCATGGATTCTAGCATTCGTACCGCGC GTATTGGTGTTTATACCCTGTTGGGCCTGCGTAAGCAGGTTCCGGA CATCAGCCCGGTCCAGTATGATATCCGCACGCTGATTAAAGCCGCG CGCACGGTTAACAACAACCAGCCGTTTCCGGGCGAGAGGCTGTTA CACCGTCTGCTTGGTAAAACGTATTACGCCCATATTCTGCCTCCGC TGCCAGATCGCACCCAGACCACCCGCGACGCGGCTGAAACCGAAT TGAAGGCCTTCCTCGGCACCGGTGGCACTGCGTTAGCAGCGGTTGG TGGTTGGCTGCAGCGTGTACGTGAGGATCTGAAAGAGCGCACCCG TAAG |
| SEQ ID NO: 17 | MCC25 | ATGAGTCCCAAGACATCAAAACCATTTCACGTGGAGAACGACACC ACCGCGGGTTATTGGTCCAACCGTCCGGAAAATACCCTGCCAGTGC CGGACATGATGGGTGCGTACATGCGTAATCGCCCGTACCCGGGCA ACCAAGTCGAGGGCCGCAAGGCATGGATTATCGGCTCTGGTATTG CAGGCCTGGCGGCGGCGTTTTACCTGATTCGCGATGGTGGCATGAA AGGTCAAGACATCACCATTTTAGATGCATTGGACGTCACTGGCGGT TCCCTGGACGGCGCGGGTAATCCGGAAGACGGGTACATCATTCGT GGTGGTCGGGAGATGAACTGGAATTATGACAACTTGTGGGATATG TTTCAAGATGTGCAAGCGCTGGAGCTCCCGGAGGGCTACTCGGTTC TGGACGAGTATCGCCAACTGAATGACGCTGATCCGAATTGGAGCA AGGCCCGTCTGATGCACAATCAGGGTGAGATCAGAGATTTCAGCA CCTTTGGTCTGACGAAACCGCAGCAGTGGGAACTCATCAGATTGTT GTTGAAGCGCAAAGAAGACCTGGACGATCTGACCATTGAAGATTA CTTTTCGCCGGGTTTCTTACAAAGCAACTTTTGGTTTCTGTGGCGTT CTATGTTCGCCTTCGAGAACTGGCAGAGCCTGTTGGAGATGAAACT CTACATGCATCGCTTTCTGGATTCTATCGACGGTTTCGCGGATATG TCCTGCCTGGTTTTCCCGAAGTATAATCAGCATGATACCTTCGTTA AACCTCTGGTGGATCATCTCAAGAAGCTGGGGGTGCAAGTTCAATT TGCGACCCGTGTTAGCGACCTGGAGATGACTGAAGATGCAGGCAA ACGTACCGTGACCGGCATTCTCGCCAGCGTTAACGGTCAAGAACA TCGTATCCCGGTAGATGAAAAAGATGTGGTGTTCGCTCTGACTGGC AGCATGACGGAGGGAACGGCCTACGGTGATATGGACCACGCACCA GTTCTGGAACGTGGACGTTCTGACCCGGGTCCGGACTCGGACTGG GCATTATGGCAGAACCTTGCGGCTAAGAGCCCGATCTTTGGCAACC CGAAAAAGTTTTACGGCGACATCGATAAATCCATGTGGGAAAGCG GTACACTGACGTGCAAACCGAGCCCACTGACCGATCGTCTGACGG AGCTTTCCGTGAACGACCCGTACAGCGGTAAGACCGTGACCGGCG GTATCATCACCTTTACCGATAGTAACTGGGTGATGAGCGTGACCTG CAACCGTCAGCCGCATTTTCCGGGCCAACCGAAGGATGTTCTGGTC TTGTGGGTCTATGCACTGCTTATGGACAAAGACGGAAACAAAGTG |

TABLE 2-continued

| SEQ ID NO: Ref | Ref Name | Amino Acid Sequence |
|---|---|---|
| | | AAGAAGCCGATGCCGGCATGTACCGGCCGCGAAATATTGGCGGAA<br>TTGTGTCACCACCTAGGCATCCCGGACGACCAGTTCGAAGCTGTGG<br>CTGCGAAGACCAAAGTTCGTCTCGCTCTGATGCCGTATATTACCAG<br>CATGTTCATGCCGCGTGCGAAGGGTGACCGTCCGCACGTTGTTCCG<br>GAGGGCTGCACTAATCTGGCGCTGATGGGTCAGTTCGTTGAGACG<br>GCCAATGACATCGTGTTCACCATGGATTCTAGCATTCGTACCGCGC<br>GTATTGGTGTTTATACCCTGTTGGGCCTGCGTAAGCAGGTTCCGGA<br>CATCAGCCCGGTCCAGTATGATATCCGCACGCTGATTAAAGCCGCG<br>CGCACGGTTAACAACAACCAGCCGTTTCCGGGCGAGAGGCTGTTA<br>CACCGTCTGCTTGGTAAAACGTATTACGCCCATATTCTGCCTCCGC<br>TGCCAGATCGCACCCAGACCACCCGCGACGCGGCTGAAACCGAAT<br>TGAAGGCCTTCCTCGGCACCGGTGGCACTGCGTTAGCAGCGGTTGG<br>TGGTTGGCTGCAGCGTGTACGTGAGGATCTGAAAGAGCGCACCCG<br>TAAG |
| SEQ ID NO: 18 | WT | ATGAGTCCCAAGACATCAAAACCATTTCACGTGGAGAACGACACC<br>ACCGCGGGTTATTGGTCCAACCGTCCGGAAAATACCCTGCCAGTGC<br>CGGACATGATGGGTGCGTACATGCGTAATCACCCGTACCCGGGCA<br>ACCAAGTCGAGGGCCGCAAGGCATGGATTATCGGCTCTGGTATTG<br>CAGGCCTGGCGGCGGCGTTTTACCTGATTCGCGATGGTGGCATGAA<br>AGGTCAAGACATCACCATTTTAGATGCATTGGACGTCACTGGCGGT<br>TCCCTGGACGGCGCGGGTAATCCGGAAGACGGGTACATCATTCGT<br>GGTGGTCGGGAGATGAACTTCAATTATGACAACTTGTGGGATATGT<br>TTCAAGATGTGCAAGCGCTGGAGCTCCCGGAGGGCTACTCGGTTCT<br>GGACGAGTATCGCCAACTGAATGACGCTGATCCGAATTGGAGCAA<br>GTCCCGTCTGATGCACAATCAGGGTGAGATCAGAGATTTCAGCAC<br>CTTTGGTCTGACGAAACCGCAGCAGTGGGAACTCATCAGATTGTTG<br>TTGAAGCGCAAAGAAGACCTGGACGATCTGACCATTGAAGATTAC<br>TTTTCGCCGGGTTTCTTACAAAGCAACTTTTGGTTTCTGTGGCGTTC<br>TATGTTCGCCTTCGAGAACTGGCAGAGCCTGTTGGAGATGAAACTC<br>TACACCCATCGCTTTCTGGATTCTATCGACGGTTTCGCGGATATGT<br>CCTGCCTGGTTTTCCCGAAGTATAATCAGCATGATACCTTCGTTAA<br>ACCTCTGGTGGATCATCTCAAGAAGCTGGGGGTGCAAGTTCAATTT<br>GCGACCCGTGTTAGCGACCTGGAGATGACTGAAGATGCAGGCAAA<br>CGTAGCGTGACCGGCATTCTCGCCAGCGTTAACGGTCAAGAACAT<br>CGTATCCCGGTAGATGAAAAAGATGTGGTGTTCGCTCTGACTGGCA<br>GCATGACGGAGGGAACGGCCTACGGTGATATGGACCACGCACCAG<br>TTATGGAACGTGGACGTTCTGACCCGGGTCCGGACTCGGACTGGG<br>CATTATGGCAGAACCTTGCGGCTAAGAGCCCGATCTTTGGCAACCC<br>GAAAAAGTTTTACGGCGACATCGATAAATCCATGTGGGAAAGCGG<br>TACACTGACGTGCAAACCGAGCCCACTGACCGATCGTCTGACGGA<br>GCTTTCCGTGAACGACCCGTACAGCGGTAAGACCGTGACCGGCGG<br>TATCATCACCTTTACCGATAGTAACTGGGTGATGAGCGTGACCTGC<br>AACCGTCAGCCGCATTTTCTGGGCCAACCGAAGGATGTTCTGGTCT<br>TGTGGGTCTATGCACTGCTTATGGACAAAGACGGAAACAAAGTGA<br>AGAAGCCGATGCCGGCATGTACCGGCCGCGAAATATTGGCGGAAT<br>TGTGTCACCACCTAGGCATCCCGGACGACCAGTTCGAAGCTGTGGC<br>TGCGAAGACCAAAGTTCGTCTCGCTCTGATGCCGTATATTACCAGC<br>ATGTTCATGCCGCGTGCGAAGGGTGACCGTCCGCACGTTGTTCCGG<br>AGGGCTGCACTAATCTGGCGCTGATGGGTCAGTTCGTTGAGACGG<br>CCAATGACATCGTGTTCACCATGGATTCTAGCATTCGTACCGCGCG<br>TATTGGTGTTTATACCCTGTTGGGCCTGCGTAAGCAGGTTCCGGAC<br>ATCAGCCCGGTCCAGTATGATATCCGCACGCTGATTAAAGCCGCGC<br>GCACGGTTAACAACAACCAGCCGTTTCCGGGCGAGAGGCTGTTAC<br>ACCGTCTGCTTGGTAAAACGTATTACGCCCATATTCTGCCTCCGCT<br>GCCAGATCGCACCCAGACCACCCGCGACGCGGCTGAAACCGAATT<br>GAAGGCCTTCCTCGGCACCGGTGGCACTGCGTTAGCAGCGGTTGGT<br>GGTTGGCTGCAGCGTGTACGTGAGGATCTGAAAGAGCGCACCCGT<br>AAG |

TABLE 3

| SEQ ID NO: Reference | Protein Name | Sequence |
|---|---|---|
| SEQ ID NO: 19 | MCC2P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNFNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD |

TABLE 3-continued

| SEQ ID NO: Reference | Protein Name | Sequence |
|---|---|---|
| | | HLKKLGVQVQFATRVSDLEMTEDAGKRTVTGILASVNGQEHRIP VDEKDVVFALTGSMTEGTAYGDMDHAPVLERGRSDPGPDSDWA LWQNLAAKSPIFGNPKKFYGDIDKSMWESGTLTCKPSPLTDRLTE LSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITSMFMPRAKGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID NO: 20 | MCC3P | MSPKTSKPFHVENDTTAGYWSNRPENTLPPPDMMGAYMRNHPY PGNQVEGRKAWIIGSGIAGLAAAFYLIRDGGMKGQDITILDALDV TGGSLDGAGNPEDGYIIRGGREMNWNYDNLWDMFQDVQALELP EGYSVLDEYRQLNDADPNWSKARLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRSVTGILASVNGQEHRIP VDEKDVVFALTGSMTEGTAYGDMDHAPVMERGRSDPGPDSDW ALWQNLAAKSPIFGNPKKFYGDIDKSMWESGTLTCKPSPLTDRLT ELSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITAMFMPRAKGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID NO: 21 | MCC6P | MSPKTSKPFHVENDTTAGYWSNRPENTLPPPDMMGAYMRNHPY PGNQVEGRKAWIIGSGIAGLAAAFYLIRDGGMKGQDITILDALDV TGGSLDGAGNPEDGYIIRGGREMNFNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRTVTGILASVNGQEHRIP VDEKDVVFALTGSMTEGTAYGDMDHAPVLERGRSDPGPDSDWA LWQNLAAKSPIFGNPKKFYGDIDKSMWESGTLTCKPSPLTDRLTE LSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITSMFMPRAKGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID NO: 22 | MCC7P | MSPKTSKPFHVENDTTAGYWSNRPENTLPVPDMMGAYMRNHPY PGNQVEGRKAWIIGSGIAGLAAAFYLIRDGGMKGQDITILDALDV TGGSLDGAGNPEDGYIIRGGREMNWNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRTVTGILASVNGQEHRIP VDEKDVVFALTGSMTEGTAYGDMDHAPVLERGRSDPGPDSDWA LWQNLAAKSPIFGNPKKFYGDIDKSMWESGTLTCKPSPLTDRLTE LSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITSMFMPRAAGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID NO: 23 | MCC8P | MSPKTSKPFHVENDTTAGYWSNRPENTLPPPDMMGAYMRNRPY PGNQVEGRKAWIIGSGIAGLAAAFYLIRDGGMKGQDITILDALDV TGGSLDGAGNPEDGYIIRGGREMNFNYDNLWDMFQDVQALELP EGYSVLDEYRQLNDADPNWSKARLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRSVTGILASVNGQEHRIP VDEKDVVFALTGSMTEGTAYGDMDHAPVLERGRSDPGPDSDWA LWQNLAAKSPIFGNPKKFYGDIDKSMWESGTLTCKPSPLTDRLKE LSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITAMFMPRAKGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID | MCC9P | MSPKTSKPFHVENDTTAGYWSNRPENTLPPPDMMGAYMRNHPY PGNQVEGRKAWIIGSGIAGLAAAFYLIRDGGMKGQDITILDALDV |

TABLE 3-continued

| SEQ ID NO: Reference | Protein Name | Sequence |
|---|---|---|
| NO: 24 | | TGGSLDGAGNPEDGYIIRGGREMNWNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRSVTGILASVNGQEHRIP VDEKDVVFALTGSMTEGTAYGDMDHAPVMERGRSDPGPDSDW ALWQNLAAKSPIFGNPKKFYGDIDKSMWESGTLTCKPSPLTDRL KELSVNDPYSGKTVTGGIITFTDSNWVMSVTCNRQPHFPGQPKD VLVLWVYALLMDKDGNKVKKPMPACTGREILAELCHHLGIPDD QFEAVAAKTKVRLALMPYITSMFMPRAAGDRPHVVPEGCTNLA LMGQFVETANDIVFTMDSSIRTARIGVYTLLGLRKQVPDISPVQY DIRTLIKAARTVNNNQPFPGERLLHRLLGKTYYAHILPPLPDRTQT TRDAAETELKAFLGTGGTALAAVGGWLQRVREDLKERTRK |
| SEQ ID NO: 25 | MCC11P | MSPKTSKPFHVENDTTAGYWSNRPENTLPVPDMMGAYMRNRPY PGNQVEGRKAWIIGSGIAGLAAAFYLIRDGGMKGQDITILDALDV TGGSLDGAGNPEDGYIIRGGREMNWNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRSVTGILASVNGQEHRIP VDEKDVVFALTGSMTEGTAYGDMDHAPVLERGRSDPGPDSDWA LWQNLAAKSPIFGNPKKFYGDIDKSMWESGTLTCKPSPLTDRLKE LSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITSMFMPRAAGDRPHVVPEGCTNLALM GQFVETANDIVFTMDSSIRTARIGVYTLLGLRKQVPDISPVQYDIR TLIKAARTVNNNQPFPGERLLHRLLGKTYYAHILPPLPDRTQTTR DAAETELKAFLGTGGTALAAVGGWLQRVREDLKERTRK |
| SEQ ID NO: 26 | MCC12P | MSPKTSKPFHVENDTTAGYWSNRPENTLPVPDMMGAYMRNHPY PGNQVEGRKAWIIGSGIAGLAAAFYLIRDGGMKGQDITILDALDV TGGSLDGAGNPEDGYIIRGGREMNWNYDNLWDMFQDVQALELP EGYSVLDEYRQLNDADPNWSKARLMHNQGEIRDFSTFGLTKPQQ WELIRLLLKRKEDLDDLTIEDYFSPGFLQSNFWFLWRSMFAFEN WQSLLEMKLYMHRFLDSIDGFADMSCLVFPKYNQHDTFVKPLV DHLKKLGVQVQFATRVSDLEMTEDAGKRTVTGILASVNGQEHRI PVDEKDVVFALTGSMTEGTAYGDMDHAPVMERGRSDPGPDSD WALWQNLAAKSPIFGNPKKFYGDIDKSMWESGTLTCKPSPLTDR LKELSVNDPYSGKTVTGGIITFTDSNWVMSVTCNRQPHFPGQPKD VLVLWVYALLMDKDGNKVKKPMPACTGREILAELCHHLGIPDD QFEAVAAKTKVRLALMPYITSMFMPRAAGDRPHVVPEGCTNLA LMGQFVETANDIVFTMDSSIRTARIGVYTLLGLRKQVPDISPVQY DIRTLIKAARTVNNNQPFPGERLLHRLLGKTYYAHILPPLPDRTQT TRDAAETELKAFLGTGGTALAAVGGWLQRVREDLKERTRK |
| SEQ ID NO: 27 | MCC14P | MSPKTSKPFHVENDTTAGYWSNRPENTLPVPDMMGAYMRNHPY PGNQVEGRKAWIIGSGIAGLAAAFYLIRDGGMKGQDITILDALDV TGGSLDGAGNPEDGYIIRGGREMNFNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYTHRFLDSIDGFADMSCLVFPKYNQHDTFVKPLVD HLKKLGVQVQFATRVSDLEMTEDAGKRSVTGILASVNGQEHRIP VDEKDVVFALTGSMTEGTAYGDMDHAPVMERGRSDPGPDSDW ALWQNLAAKSPIFGNPKKFYGDIDKSMWESGTLTCKPSPLTDRL KELSVNDPYSGKTVTGGIITFTDSNWVMSVTCNRQPHFLGQPKD VLVLWVYALLMDKDGNKVKKPMPACTGREILAELCHHLGIPDD QFEAVAAKTKVRLALMPYITSMFMPRAKGDRPHVVPEGCTNLA LMGQFVETANDIVFTMDSSIRTARIGVYTLLGLRKQVPDISPVQY DIRTLIKAARTVNNNQPFPGERLLHRLLGKTYYAHILPPLPDRTQT TRDAAETELKAFLGTGGTALAAVGGWLQRVREDLKERTRK |
| SEQ ID NO: 28 | MCC15P | MSPKTSKPFHVENDTTAGYWSNRPENTLPVPDMMGAYMRNHPY PGNQVEGRKAWIIGSGIAGLAAAFYLIRDGGMKGQDITILDALDV TGGSLDGAGNPEDGYIIRGGREMNWNYDNLWDMFQDVQALELP EGYSVLDEYRQLNDADPNWSKSRLMHNQGEIRDFSTFGLTKPQQ WELIRLLLKRKEDLDDLTIEDYFSPGFLQSNFWFLWRSMFAFEN WQSLLEMKLYMHRFLDSIDGFADMSCLVFPKYNQHDTFVKPLV DHLKKLGVQVQFATRVSDLEMTEDAGKRSVTGILASVNGQEHRI PVDEKDVVFALTGSMTEGTAYGDMDHAPVLERGRSDPGPDSDW ALWQNLAAKSPIFGNPKKFYGDIDKSMWESGTLTCKPSPLTDRLT ELSVNDPYSGKTVTGGIITFTDSNWVMSVTCNRQPHFPGQPKDVL VLWVYALLMDKDGNKVKKPMPACTGREILAELCHHLGIPDDQF EAVAAKTKVRLALMPYITSMFMPRAKGDRPHVVPEGCTNLALM |

TABLE 3-continued

| SEQ ID NO: Reference | Protein Name | Sequence |
|---|---|---|
| | | GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 29 | MCC17P | MSPKTSKPFHVENDTTAGYWSNRPENTLPVPDMMGAYMRNHPY<br>PGNQVEGRKAWIIGSGIAGLAAAFYLIRDGGMKGQDITILDALDV<br>TGGSLDGAGNPEDGYIIRGGREMNFNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRSVTGILASVNGQEHRIP<br>VDEKDVVFALTGSMTEGTAYGDMDHAPVMERGRSDPGPDSDW<br>ALWQNLAAKSPIFGNPKKFYGDIDKSMWESGTLTCKPSPLTDRL<br>KELSVNDPYSGKTVTGGIITFTDSNWVMSVTCNRQPHFPGQPKD<br>VLVLWVYALLMDKDGNKVKKPMPACTGREILAELCHHLGIPDD<br>QFEAVAAKTKVRLALMPYITSMFMPRAAGDRPHVVPEGCTNLA<br>LMGQFVETANDIVFTMDSSIRTARIGVYTLLGLRKQVPDISPVQY<br>DIRTLIKAARTVNNNQPFPGERLLHRLLGKTYYAHILPPLPDRTQT<br>TRDAAETELKAFLGTGGTALAAVGGWLQRVREDLKERTRK |
| SEQ ID NO: 30 | MCC18P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNWNYDNLWDMFQDVQALELP<br>EGYSVLDEYRQLNDADPNWSKARLMHNQGEIRDFSTFGLTKPQQ<br>WELIRLLLKRKEDLDDLTIEDYFSPGFLQSNFWFLWRSMFAFEN<br>WQSLLEMKLYMHRFLDSIDGFADMSCLVFPKYNQHDTFVKPLV<br>DHLKKLGVQVQFATRVSDLEMTEDAGKRTVTGILASVNGQEHRI<br>PVDEKDVVFALTGSMTEGTAYGDMDHAPVLERGRSDPGPDSDW<br>ALWQNLAAKSPIFGNPKKFYGDIDKSMWESGTLTCKPSPLTDRLT<br>ELSVNDPYSGKTVTGGIITFTDSNWVMSVTCNRQPHFPGQPKDVL<br>VLWVYALLMDKDGNKVKKPMPACTGREILAELCHHLGIPDDQF<br>EAVAAKTKVRLALMPYITSMFMPRAKGDRPHVVPEGCTNLALM<br>GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 31 | MCC19P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNWNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRTVTGILASVNGQEHRIP<br>VDEKDVVFALTGSMTEGTAYGDMDHAPVMERGRSDPGPDSDW<br>ALWQNLAAKSPIFGNPKKFYGDIDKSMWESGTLTCKPSPLTDRL<br>KELSVNDPYSGKTVTGGIITFTDSNWVMSVTCNRQPHFPGQPKD<br>VLVLWVYALLMDKDGNKVKKPMPACTGREILAELCHHLGIPDD<br>QFEAVAAKTKVRLALMPYITSMFMPRAKGDRPHVVPEGCTNLA<br>LMGQFVETANDIVFTMDSSIRTARIGVYTLLGLRKQVPDISPVQY<br>DIRTLIKAARTVNNNQPFPGERLLHRLLGKTYYAHILPPLPDRTQT<br>TRDAAETELKAFLGTGGTALAAVGGWLQRVREDLKERTRK |
| SEQ ID NO: 32 | MCC20P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNFNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRSVTGILASVNGQEHRIP<br>VDEKDVVFALTGSMTEGTAYGDMDHAPVMERGRSDPGPDSDW<br>ALWQNLAAKSPIFGNPKKFYGDIDKSMWESGTLTCKPSPLTDRLT<br>ELSVNDPYSGKTVTGGIITFTDSNWVMSVTCNRQPHFPGQPKDVL<br>VLWVYALLMDKDGNKVKKPMPACTGREILAELCHHLGIPDDQF<br>EAVAAKTKVRLALMPYITSMFMPRAKGDRPHVVPEGCTNLALM<br>GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 33 | MCC21P | MSPKTSKPFHVENDTTAGYWSNRPENTLPVPDMMGAYMRNHPY<br>PGNQVEGRKAWIIGSGIAGLAAAFYLIRDGGMKGQDITILDALDV<br>TGGSLDGAGNPEDGYIIRGGREMNFNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRSVTGILASVNGQEHRIP<br>VDEKDVVFALTGSMTEGTAYGDMDHAPVLERGRSDPGPDSDWA |

TABLE 3-continued

| SEQ ID NO: Reference | Protein Name | Sequence |
|---|---|---|
| | | LWQNLAAKSPIFGNPKKFYGDIDKSMWESGTLTCKPSPLTDRLTE<br>LSVNDPYSGKTVTGGIITFTDSNWVMSVTCNRQPHFPGQPKDVL<br>VLWVYALLMDKDGNKVKKPMPACTGREILAELCHHLGIPDDQF<br>EAVAAKTKVRLALMPYITSMFMPRAKGDRPHVVPEGCTNLALM<br>GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 34 | MCC22P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNWNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRSVTGILASVNGQEHRIP<br>VDEKDVVFALTGSMTEGTAYGDMDHAPVMERGRSDPGPDSDW<br>ALWQNLAAKSPIFGNPKKFYGDIDKSMWESGTLTCKPSPLTDRLT<br>ELSVNDPYSGKTVTGGIITFTDSNWVMSVTCNRQPHFPGQPKDVL<br>VLWVYALLMDKDGNKVKKPMPACTGREILAELCHHLGIPDDQF<br>EAVAAKTKVRLALMPYITAMFMPRAKGDRPHVVPEGCTNLALM<br>GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 35 | MCC25P | MSPKTSKPFHVENDTTAGYWSNRPENTLPVPDMMGAYMRNRPY<br>PGNQVEGRKAWIIGSGIAGLAAAFYLIRDGGMKGQDITILDALDV<br>TGGSLDGAGNPEDGYIIRGGREMNWNYDNLWDMFQDVQALELP<br>EGYSVLDEYRQLNDADPNWSKARLMHNQGEIRDFSTFGLTKPQQ<br>WELIRLLLKRKEDLDDLTIEDYFSPGFLQSNFWFLWRSMFAFEN<br>WQSLLEMKLYMHRFLDSIDGFADMSCLVFPKYNQHDTFVKPLV<br>DHLKKLGVQVQFATRVSDLEMTEDAGKRTVTGILASVNGQEHRI<br>PVDEKDVVFALTGSMTEGTAYGDMDHAPVLERGRSDPGPDSDW<br>ALWQNLAAKSPIFGNPKKFYGDIDKSMWESGTLTCKPSPLTDRLT<br>ELSVNDPYSGKTVTGGIITFTDSNWVMSVTCNRQPHFPGQPKDVL<br>VLWVYALLMDKDGNKVKKPMPACTGREILAELCHHLGIPDDQF<br>EAVAAKTKVRLALMPYITSMFMPRAKGDRPHVVPEGCTNLALM<br>GQFVETANDIVFTMDSSIRTARIGVYTLLGLRKQVPDISPVQYDIR<br>TLIKAARTVNNNQPFPGERLLHRLLGKTYYAHILPPLPDRTQTTR<br>DAAETELKAFLGTGGTALAAVGGWLQRVREDLKERTRK |
| SEQ ID NO: 36 | WTP | MSPKTSKPFHVENDTTAGYWSNRPENTLPVPDMMGAYMRNHPY<br>PGNQVEGRKAWIIGSGIAGLAAAFYLIRDGGMKGQDITILDALDV<br>TGGSLDGAGNPEDGYIIRGGREMNFNYDNLWDMFQDVQALELP<br>EGYSVLDEYRQLNDADPNWSKSRLMHNQGEIRDFSTFGLTKPQQ<br>WELIRLLLKRKEDLDDLTIEDYFSPGFLQSNFWFLWRSMFAFEN<br>WQSLLEMKLYTHRFLDSIDGFADMSCLVFPKYNQHDTFVKPLVD<br>HLKKLGVQVQFATRVSDLEMTEDAGKRSVTGILASVNGQEHRIP<br>VDEKDVVFALTGSMTEGTAYGDMDHAPVMERGRSDPGPDSDW<br>ALWQNLAAKSPIFGNPKKFYGDIDKSMWESGTLTCKPSPLTDRLT<br>ELSVNDPYSGKTVTGGIITFTDSNWVMSVTCNRQPHFLGQPKDV<br>LVLWVYALLMDKDGNKVKKPMPACTGREILAELCHHLGIPDDQ<br>FEAVAAKTKVRLALMPYITSMFMPRAKGDRPHVVPEGCTNLAL<br>MGQFVETANDIVFTMDSSIRTARIGVYTLLGLRKQVPDISPVQYDI<br>RTLIKAARTVNNNQPFPGERLLHRLLGKTYYAHILPPLPDRTQTT<br>RDAAETELKAFLGTGGTALAAVGGWLQRVREDLKERTRK |

Accordingly, some aspects include a composition of a recombinant nucleic acid having at least 65% homology with any of SEQ ID NOs: 1-17.

In some aspects, the composition of recombinant has at least 75% homology with any of SEQ. ID Nos. 1-17.

In some aspects, the composition of recombinant has at least 80% homology with any of SEQ. ID Nos. 1-17.

In some aspects, the composition of recombinant has at least 85% homology with any of SEQ. ID Nos. 1-17.

In some aspects, the composition of recombinant has at least 90% homology with any of SEQ. ID Nos. 1-17.

In some aspects, the composition of recombinant has at least 95% homology with any of SEQ. ID Nos. 1-17.

In some aspects, the composition of recombinant has at least 99% homology with any of SEQ. ID Nos. 1-17.

In some aspects, the composition of recombinant is any of SEQ. ID Nos. 1-17.

Turning to FIG. 4, a chart is provided that identifies the position and identity of the amino acid substitutions of selected variant oleic acid hydratase enzymes, in accordance with aspects hereof. The chart identifies the wild type amino acid at a specified position and the amino acid that is substituted at that position. For example, the chart shows wild type valine at position 30 may be substituted with a proline in some aspects. The wild type histidine at position 41 may be substituted with an arginine. The wild type phenylalanine at position 113 may be substituted with a tryptophan. The wild type serine at position 153 may be substituted with an alanine. The wild type threonine at position 230 may be substituted with a methionine. The wild type cysteine at position 245 may be substituted with an alanine. The wild type serine at position 291 may be substituted with a threonine. The wild type methionine at position 336 may be substituted with a leucine. The wild type threonine at position 394 may be substituted with a lysine. The wild type leucine at position 432 may be substituted with a proline. The wild type serine at position 510 may be substituted with an alanine. The wild type lysine at position 508 may be substituted with an alanine. In the chart of FIG. 4, an 'x' in a given cell indicates the presence of the substitution mutation in the respective variant oleic acid hydratase enzyme. For example, MCC6P (i.e., SEQ ID NO: 21) includes the V30P, S291T, M336L, and L432P substitutions.

With reference to Table 1, Table 2, and FIG. 4, some aspects described herein include a bacterial cell including at least one recombinant plasmid including a region having at least 85% homology with any of SEQ ID NOs: 1-17. The bacterial cell can include a promoter region that induces transcription of at least a portion of the region having at least 85% homology with any of SEQ ID NOs: 1-17. In some aspects, the protein expressed by transcription and translation of the region having at least 85% homology with any of SEQ ID NOs: 1-17 includes at least two of: a proline at position 30; an arginine at position 41; a tryptophan at position 113; an alanine at position 153; a methionine at position 230; a threonine at position 291; a leucine at position 336; a lysine at position 394; a proline at position 432; an alanine at position 501; or an alanine at position 508.

Some aspects described herein are directed to a composition of at least one recombinant oleic acid hydratase protein. For example, at least one aspect includes recombinant protein having at least 85% homology with any of SEQ ID NOs: 18-35. In some aspects, the recombinant protein includes at least two of: a proline at position 30; an arginine at position 41; a tryptophan at position 113; an alanine at position 153; a methionine at position 230; a threonine at position 291; a leucine at position 336; a lysine at position 394; a proline at position 432; an alanine at position 501; or an alanine at position 508.

In some aspects, the recombinant protein includes at least one of a tryptophan at position 113; a leucine at position 336; or a proline at position 432. Some aspects additionally include at least one of: an arginine at position 41; a threonine at position 291; or a lysine at position 394. Some aspects additionally include at least one of: a proline at position 30; an alanine at position 153; a methionine at position 230; an alanine at position 501; or an alanine at position 508.

Figure 5:
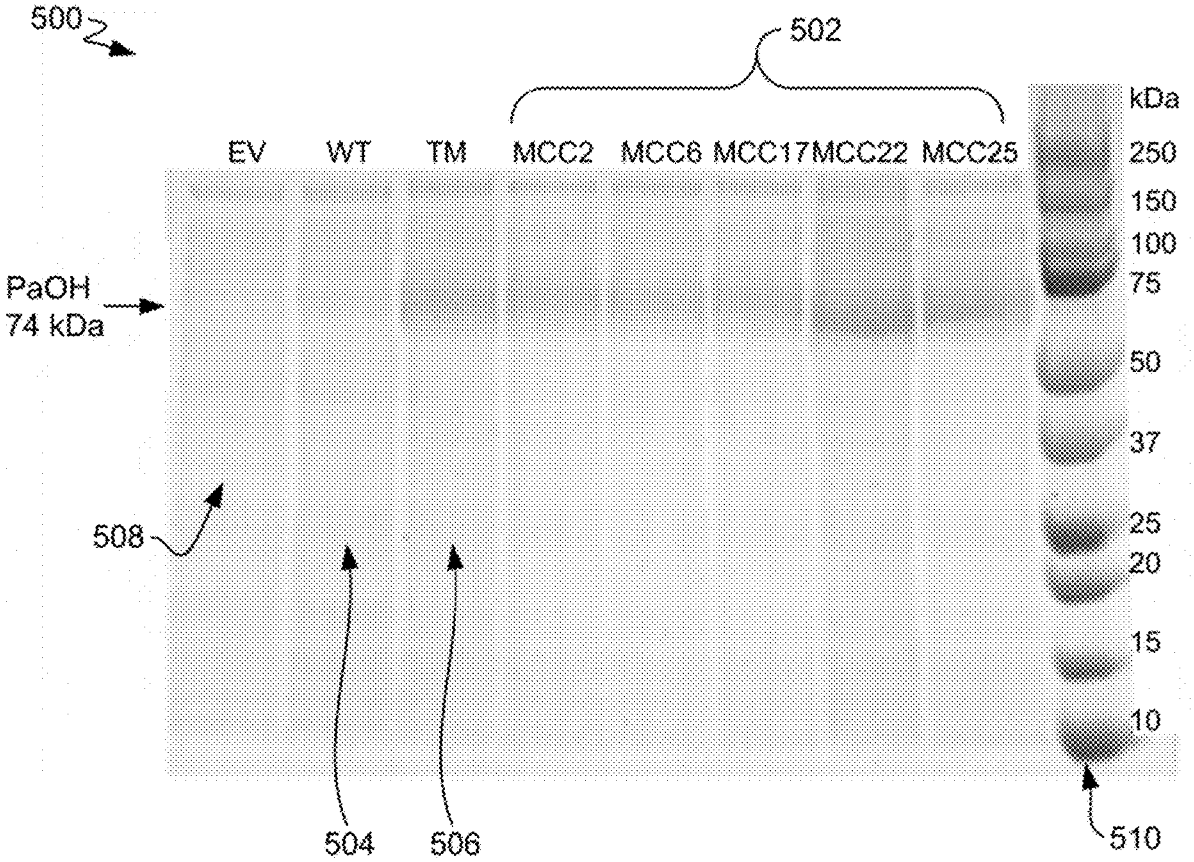
FIG. 5 is an example SDS-PAGE analysis of selected examples of mutant oleic acid hydratase, in accordance with aspects described herein.

Turning to FIG. 5, the expression level of the target enzyme was also analyzed for all variants, with results of SDS-PAGE analysis and quantification of the target protein (e.g., the mutant oleic acid hydratase). For example, FIG. 5 depicts an image of a sample SDS-PAGE including a protein ladder 510, MCC2P, MCC6P, MCC17P, MCC22P, and MCC25P (collectively 502). Additionally included in FIG. 5 are controls WT protein 504, TM protein 506, and EV 508. As shown, the wild type oleic acid hydratase is approximately 74 kilo Daltons (kDa) in size. Similarly, the TM protein, MCC2P, MCC6P, MCC17P, MCC22P, and MCC25P are approximately 74 kilo Daltons (kDa) in size. Additionally, as depicted, the SDS-PAGE confirmed that the EV did not produce a protein of relevance.

The SDS-PAGE of FIG. 5 was quantified and the results are shown in Table 4 (below). Based on the quantification of the SDS-PAGE, the comparative performance of variants MCC2P, 6P, 17P, and 25P could be attributed to increased expression levels within the bacterial cell. The comparatively better performance of variants MCC22 may be attributed to both the elevated protein expression level and specific activity.

TABLE 4

| VARIANT | PEAK AREA OF TARGET PROTEIN | PEAK AREA OF TARGET PROTEIN (BACKGROUND SUBTRACTED) | EXPRESSION LEVEL (COMPARED WITH WILD TYPE ENZYME) |
|---|---|---|---|
| EV | 1435.196 | 0 | |
| WTP | 3310.288 | 1875.092 | 1.0 |
| TMP | 10861.969 | 9426.773 | 5.0 |
| MCC2P | 11888.434 | 10453.238 | 5.6 |
| MCC6P | 11326.584 | 9891.388 | 5.3 |
| MCC17P | 11802.756 | 10367.56 | 5.5 |
| MCC22P | 18547.626 | 17112.43 | 9.1 |
| MCC25P | 16095.454 | 14660.258 | 7.8 |

Biocatalyzed Production of (R)-10-HSA

Figure 6:
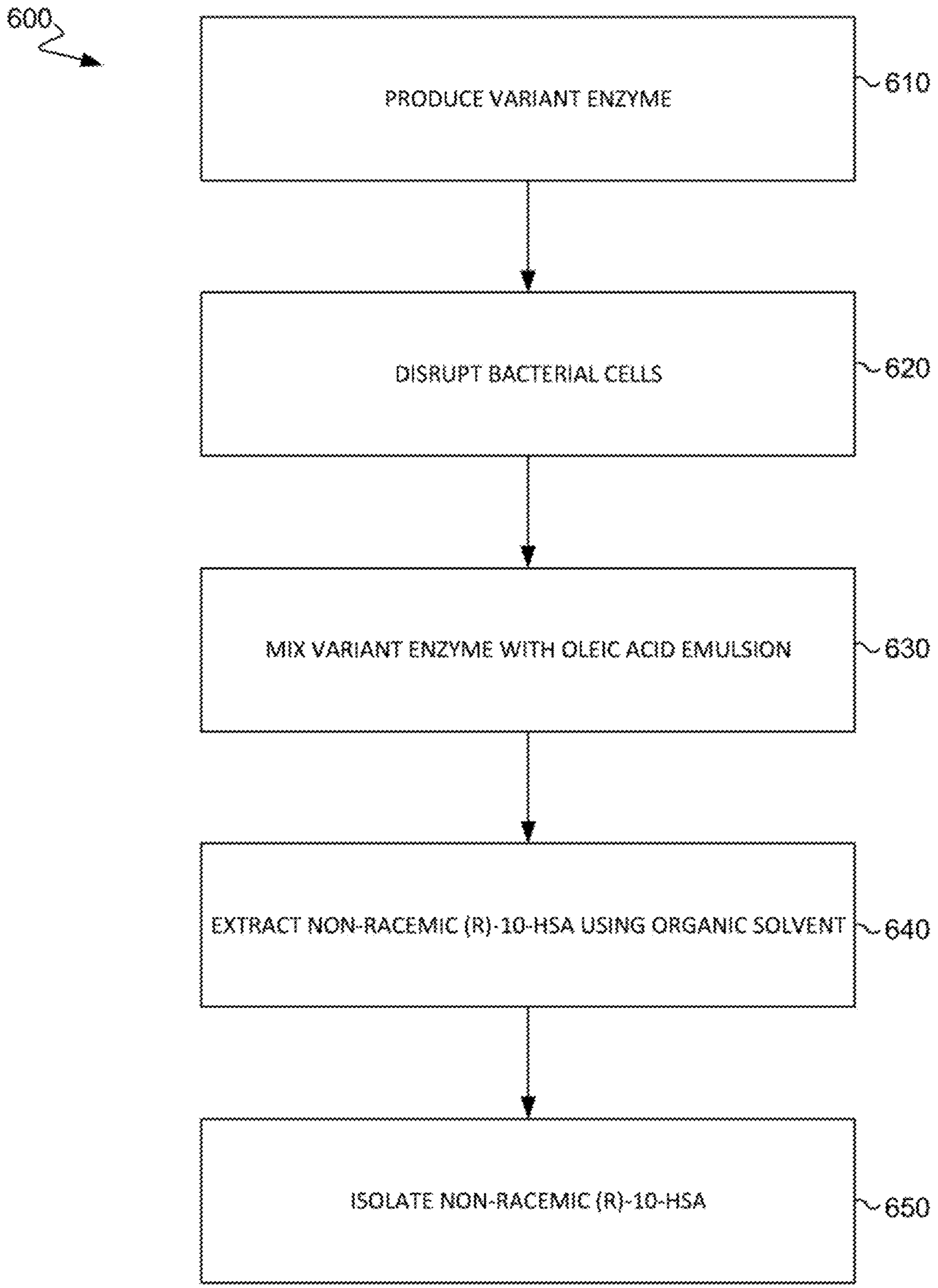
FIG. 6 is an example method for the biocatalzyed production of (R)-10-hydroxystearic acid, in accordance with aspects described herein.

Turning to FIG. 6, an example process for the biocatalyzed production of (R)-10-HSA is depicted in method 600. Generally, method 600 includes the production of one or more mutant oleic acid hydratase enzymes (e.g., any protein of SEQ ID NO: 19-35) using a plurality of bacterial cells. The bacterial cells are disrupted to release the one or more mutant oleic acid hydratase enzymes. The one or more mutant oleic acid hydratase enzymes are mixed with an emulsification including oleic acid. The one or more mutant oleic acid hydratase enzymes catalyze reaction of the oleic acid to (R)-10-HSA. The (R)-10-HSA can be extracted from the emulsified mix including the one or more mutant oleic acid hydratase enzymes using an organic solvent. (R)-10-HSA can then be crystalized and dried using traditional methods. Some embodiments of method 600 begin with block 610.

At block 610, method 600 includes production of the enzyme. The enzyme can be any protein of SEQ ID NO: 19-35. For example, a recombinant plasmid containing any one of SEQ ID NO: 1-17 can be transferred into a competent bacterial cell. The transformation may be accomplished by electroporation or chemical stimulation of a plurality of competent bacterial cell. Chemical transformation methods typically involve the use of calcium chloride or other cationic agents to increase the permeability of the bacterial cell membrane. Electroporation involves applying an electrical field to the bacterial cell, which causes temporary pores to form in the membrane and allows for the uptake of the plasmid. Once the bacterial cell is competent, it can be mixed with the recombinant plasmid and subjected to transformation conditions. The recombinant plasmid typically contains a selectable marker, such as an antibiotic resistance gene, to allow for selection of transformed cells. The plasmid may also contain regulatory elements, such as promoters and terminators, to control the expression of the one or more mutant oleic acid hydratase enzymes.

At block 620, method 600 includes disruption of the transformed bacterial cells that express one or more mutant oleic acid hydratase enzyme. For example, the bacterial cells may be subjected to mechanical disruption, such as sonication, bead beating, or homogenization. This step involves applying mechanical force to the bacterial cells to physically break apart the cell wall and membrane, allowing the cytoplasmic proteins to be released into the surrounding solution. Said another way, a sonicator may be used to lyse the transformed bacterial cells to release one or more proteins of SEQ ID NO: 19-35.

In some embodiments, the mechanical disruption step may be followed by a chemical lysis step. This may involve the use of detergents, such as Triton X-100 or sodium dodecyl sulfate (SDS), to further disrupt the cell membrane and release the mutant oleic acid hydratase enzyme.

After lysis, the released oleic acid hydratase enzyme proteins can be separated from cellular debris using various methods, such as centrifugation or chromatography. Alternatively, some embodiments of block 604 omit separation of the mutant oleic acid hydratase enzyme from the cellular debris.

At block 630, method 600 includes mixing one or more proteins of SEQ ID NO: 19-35 with oleic acid. For example, the lysate of block 620 may be mixed with an emulsion of oleic acid, buffer, and a surfactant. The mixing may be facilitated by any suitable means. For example, mixing may be facilitated in some aspects by stirring, vibration, rocking, or any other means.

At block 640, method 600 includes extracting non-racemic (R)-10-HSA using an organic solvent. For example, an organic solvent may be added to the reaction vessel and mixed via the same or similar means as used to mix the lysate and the emulsion of oleic acid, buffer, and surfactant. In some aspects, the organic solvent is ethyl acetate.

At block 650, method 600 includes isolating at least a portion of the non-racemic (R)-10-HSA. In some aspects, the non-racemic (R)-10-HSA may be isolated from the organic solvent using crystallization. For example, the organic solvent containing (R)-10-HSA is first concentrated using various techniques such as evaporation or distillation. The concentrated solution is then allowed to cool to a temperature below the melting point of (R)-10-HSA.

As the solution cools, (R)-10-HSA begins to crystallize and precipitate out of the solution. The crystals are then separated from the remaining solution using various methods such as filtration or centrifugation. The separated crystals can be washed with a suitable solvent to remove any impurities that may be adsorbed onto the crystal surface. The washed crystals are then dried to remove any remaining solvent, producing a purified (R)-10-HSA.

In some aspects, the crystallization process may be enhanced by the use of various techniques such as seeding, where small crystals of (R)-10-HSA are introduced into the solution to promote the growth of larger crystals.

The method of the present invention for isolating (R)-10-HSA from an organic solvent can be used for a variety of applications, including the production of various industrial products such as lubricants, adhesives, and coatings.

Figure 7:
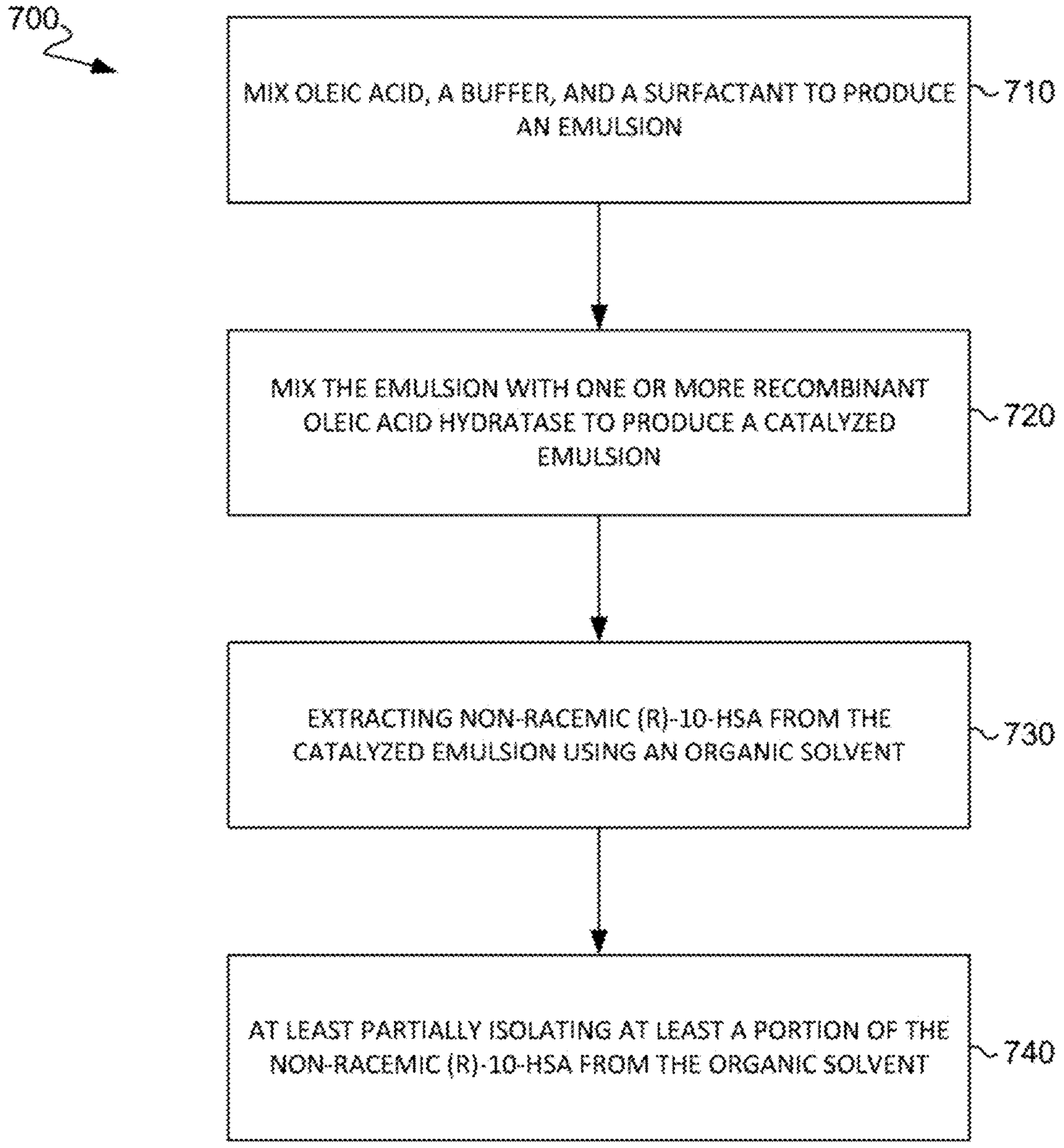
FIG. 7 is another example method for the biocatalzyed production of (R)-10-hydroxystearic acid, in accordance with aspects described herein

Turning to FIG. 7, another example method 700 for the biocatalyzed conversion of oleic acid to non-racemic (R)-10-HSA is depicted in accordance with embodiments described herein. Some embodiments of method 700 begin with block 710.

At block 710, method 700 includes mixing oleic acid, a buffer, and a surfactant to produce an emulsion. In some aspects, the buffer includes phosphate and has a pH in a range of 4.5-7.0. In some aspects, the organic solvent includes ethyl acetate. The surfactant may include a monoglyceride, diglyceride, an ester of polyethylene glycol, or an ester of sorbitan. For example, in some aspects, the surfactant comprises polysorbate-80. The production of the emulsion may be facilitated by any suitable means. For example, emulsification may be facilitated in some aspects by stirring, vibration (e.g., sonication), rocking, or any other means.

At block 720, method 700 includes mixing the emulsion with at least one mutant oleic acid hydratase enzyme. For example, the mutant oleic acid hydratase enzyme may have at least 65% homology with any of SEQ ID NO: 19-35.

In some aspects, the mutant oleic acid hydratase enzyme may have at least 70% homology with any of SEQ ID NO: 19-35.

In some aspects, the mutant oleic acid hydratase enzyme may have at least 75% homology with any of SEQ ID NO: 19-35.

In some aspects, the mutant oleic acid hydratase enzyme may have at least 80% homology with any of SEQ ID NO: 19-35.

In some aspects, the mutant oleic acid hydratase enzyme may have at least 85% homology with any of SEQ ID NO: 19-35.

In some aspects, the mutant oleic acid hydratase enzyme may have at least 90% homology with any of SEQ ID NO: 19-35.

In some aspects, the mutant oleic acid hydratase enzyme may have at least 95% homology with any of SEQ ID NO: 19-35.

In some aspects, the mutant oleic acid hydratase enzyme may have at least 99% homology with any of SEQ ID NO: 19-35.

In some aspects, the mutant oleic acid hydratase enzyme is homologous with any of SEQ ID NO: 19-35.

The mixing of the emulsion with the at least one mutant oleic acid hydratase enzyme produces a catalyzed emulsion. The mixing may be facilitated by any suitable means. For example, mixing may be facilitated in some aspects by stirring, vibration, rocking, or any other means.

At block 730, method 700 includes extracting non-racemic (R)-10-HSA from the catalyzed emulsion using an organic solvent. For example, an organic solvent may be added to the reaction vessel and mixed via the same or similar means as used to mix the mutant oleic acid hydratase enzyme and the emulsion of oleic acid, buffer, and surfactant. In some aspects, the organic solvent is ethyl acetate.

At block 740, method 700 includes at least partially isolating at least a portion of the non-racemic (R)-10-HSA from the organic solvent. In some aspects, the non-racemic (R)-10-HSA may be isolated from the organic solvent using crystallization. For example, the organic solvent containing (R)-10-HSA is first concentrated using various techniques such as evaporation or distillation. The concentrated solution is then allowed to cool to a temperature below the melting point of (R)-10-HSA.

As the solution cools, (R)-10-HSA begins to crystallize and precipitate out of the solution. The crystals are then separated from the remaining solution using various methods such as filtration or centrifugation. The separated crystals can be washed with a suitable solvent to remove any impurities that may be adsorbed onto the crystal surface. The washed crystals are then dried to remove any remaining solvent, producing a purified (R)-10-HSA.

In some aspects, the crystallization process may be enhanced by the use of various techniques such as seeding, where small crystals of (R)-10-HSA are introduced into the solution to promote the growth of larger crystals.

Some aspects of block 740 further include mixing (R)-10-HSA with lithium or any other metal (e.g., alkali metal, alkaline earth metals, transition metals, metalloids, or post-transition metals) to produce a non-racemic thickening agent that includes (R)-10-HSA. In at least one aspect, the non-racemic (R)-10-HSA is mixed with lithium (Li) to produce Li(R)-10-HSA.

From the foregoing, it will be seen that this invention is one well adapted to attain all the ends and objects herein-above set forth together with other advantages which are obvious and which are inherent to the structure.

It will be understood that certain features and subcombinations are of utility and may be employed without reference to other features and subcombinations. This is contemplated by and is within the scope of the claims.

While specific elements and steps are discussed in connection to one another, it is understood that any element and/or steps provided herein is contemplated as being combinable with any other elements and/or steps regardless of explicit provision of the same while still being within the scope provided herein. Since many possible embodiments may be made of the disclosure without departing from the scope thereof, it is to be understood that all matter herein set forth or shown in the accompanying drawings is to be interpreted as illustrative and not in a limiting sense.

As used herein and in connection with the claims listed hereinafter, the terminology “any of clauses” or similar variations of said terminology is intended to be interpreted such that features of claims/clauses may be combined in any combination. For example, an exemplary clause 4 may indicate the method/apparatus of any of clauses 1 through 3, which is intended to be interpreted such that features of clause 1 and clause 4 may be combined, elements of clause 2 and clause 4 may be combined, elements of clause 3 and 4 may be combined, elements of clauses 1, 2, and 4 may be combined, elements of clauses 2, 3, and 4 may be combined, elements of clauses 1, 2, 3, and 4 may be combined, and/or other variations. Further, the terminology “any of clauses” or similar variations of said terminology is intended to include “any one of clauses” or other variations of such terminology, as indicated by some of the examples provided above.

Clause 1. A biocatalyzed method for the conversion of oleic acid to non-racemic (R)-10-hydroxystearic acid (10-HSA) comprising: mixing oleic acid, a buffer, and a surfactant to produce an emulsion; mixing the emulsion with an enzyme having at least 85% homology with any of SEQ ID. No. 19-35 to produce a catalyzed emulsion; extracting non-racemic (R)-10-HSA from the catalyzed emulsion using an organic solvent; and at least partially isolating at least a portion of the non-racemic (R)-10-HSA from the organic solvent.

Clause 2. The biocatalyzed method of clause 1, wherein the buffer includes phosphate and has a pH in a range of 4.5-7.0.

Clause 3. The biocatalyzed method of clause 1 or 2, wherein the emulsion includes less than or equal to 25% oleic acid by volume.

Clause 4. The biocatalyzed method of any of clauses 1-3, wherein the organic solvent includes ethyl acetate.

Clause 5. The biocatalyzed method of any of clauses 1-4, wherein the surfactant comprises a monoglycerid, diglyceride, an ester of polyethylene glycol, or an ester of sorbitan.

Clause 6. The biocatalyzed method of clause 5, wherein the surfactant comprises polysorbate-80.

Clause 7. The biocatalyzed method of any of clauses 1-6, further comprising lysing bacterial cells that have recombinantly expressed the enzyme.

Clause 8. The biocatalyzed method of clause 7, wherein the enzyme, obtained via the lysing, is mixed with the emulsion without purification from cellular debris.

Clause 9. The biocatalyzed method of any of clauses 1-8, wherein the non-racemic (R)-10-HSA is 80% or greater in enantiomeric excess.

Clause 10. The biocatalyzed method of any of clauses 1-9, wherein the enzyme includes a proline at position 432.

Clause 11. A bacterial cell including at least one recombinant plasmid including a region having at least 85% homology with any of SEQ IDs. No. 1-17.

Clause 12. The bacterial cell of clause 11, wherein the at least one recombinant plasmid includes a promoter region that induces transcription of at least a portion of the region having at least 85% homology with any of SEQ IDs. No. 1-17.

Clause 13. The bacterial cell of clause 11 or 12, wherein the bacterial cell further includes a recombinant protein generated by transcription and translation of the region having at least 85% homology with any of SEQ IDs. No. 1-17.

Clause 14. The bacterial cell of clause 13, wherein the protein includes at least two of: a proline at position 30; an arginine at position 41; a tryptophan at position 113; an alanine at position 153; a methionine at position 230; a threonine at position 291; a leucine at position 336; a lysine at position 394; a proline at position 432; an alanine at position 501; or an alanine at position 508.

Clause 15. A composition comprising a recombinant nucleic acid having at least 85% homology with any of SEQ ID. No. 1-17.

Clause 16. The composition of clause 15, wherein the recombinant nucleic acid has at least 90% homology with any of SEQ ID. No. 1-17.

Clause 17. The composition of clause 15, wherein the recombinant nucleic acid has at least 95% homology with any of SEQ ID. No. 1-17.

Clause 18. A composition comprising recombinant protein having at least 85% homology with any of SEQ ID. No. 19-35.

Clause 19. The composition of any of clauses 15-18, wherein the recombinant protein includes at least two of: a proline at position 30; an arginine at position 41; a tryptophan at position 113; an alanine at position 153; a methionine at position 230; a threonine at position 291; a leucine at position 336; a lysine at position 394; a proline at position 432; an alanine at position 501; or an alanine at position 508.

Clause 20. The composition of any of clauses 15-18, wherein the recombinant protein includes at least one of: a tryptophan at position 113; a leucine at position 336; or a proline at position 432.

Clause 22. The composition of any of clauses 15-18 or 20, wherein the protein also includes at least one of: an arginine at position 41; a threonine at position 291; or a lysine at position 394.

Clause 23. The composition of any of clauses 15-18, 20, or 21, wherein the protein also includes at least one of: a proline at position 30; an alanine at position 153; a methionine at position 230; an alanine at position 501; or an alanine at position 508.

We claim:

1. A biocatalyzed method for the conversion of oleic acid to non-racemic (R)-10-hydroxystearic acid (10-HSA) comprising: mixing oleic acid, a buffer, and a surfactant to produce an emulsion; mixing the emulsion with an enzyme having at least 90% homology with any of SEQ ID. No. 19-35 to produce a catalyzed emulsion; extracting non-racemic (R)-10-HSA from the catalyzed emulsion using an organic solvent; and at least partially isolating at least a portion of the non-racemic (R)-10-HSA from the organic solvent, wherein the enzyme is oleic acid hydratase.

2. The biocatalyzed method of claim 1, wherein the buffer includes phosphate and has a pH in a range of 4.5-7.0.

3. The method of claim 1, wherein the emulsion includes less than or equal to 25% oleic acid by volume.

4. The method of claim 1, wherein the organic solvent includes ethyl acetate.

5. The method of claim 1, wherein the surfactant comprises a monoglycerid, diglyceride, an ester of polyethylene glycol, or an ester of sorbitan.

6. The method of claim 5, wherein the surfactant comprises polysorbate-80.

7. The method of claim 1, further comprising:

lysing bacterial cells that have expressed the enzyme.

8. The method of claim 7, wherein the enzyme, obtained via said lysing, is mixed with the emulsion without purification from cellular debris.

9. The method of claim 8, wherein the non-racemic (R)-10-HSA is 80% or greater in enantiomeric excess.

10. The method of claim 1, wherein the enzyme includes a proline at position 432.

* * * * *

SEQUENCE LISTING

```
Sequence total quantity: 36
SEQ ID NO: 1           moltype = DNA  length = 1962
FEATURE                Location/Qualifiers
```

```
source                  1..1962
                        mol_type = other DNA
                        organism = synthetic construct
SEQUENCE: 1
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962

SEQ ID NO: 2            moltype = DNA  length = 1962
FEATURE                 Location/Qualifiers
source                  1..1962
                        mol_type = other DNA
                        organism = synthetic construct
SEQUENCE: 2
atgagtccca agacatcaaa accatttcac gtggagaacg acaccaccgc gggttattgg  60
tccaaccgtc cggaaaatac cctgccaccg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaaggccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
gccatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962

SEQ ID NO: 3            moltype = DNA  length = 1962
```

```
FEATURE                 Location/Qualifiers
source                  1..1962
                        mol_type = other DNA
                        organism = synthetic construct
SEQUENCE: 3
atgagtccca agacatcaaa accatttcac gtggagaacg acaccaccgc gggttattgg  60
tccaaccgtc cggaaaatac cctgccaccg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962

SEQ ID NO: 4            moltype = DNA  length = 1962
FEATURE                 Location/Qualifiers
source                  1..1962
                        mol_type = other DNA
                        organism = synthetic construct
SEQUENCE: 4
atgagtccca agacatcaaa accatttcac gtggagaacg acaccaccgc gggttattgg  60
tccaaccgtc cggaaaatac cctgccagtg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc ggcgggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962
```

```
SEQ ID NO: 5            moltype = DNA  length = 1962
FEATURE                 Location/Qualifiers
source                  1..1962
                        mol_type = other DNA
                        organism = synthetic construct
SEQUENCE: 5
atgagtccca agacatcaaa accatttcac gtggagaacg acaccaccgc gggttattgg  60
tccaaccgtc cggaaaatac cctgccaccg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaaggccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
gccatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962

SEQ ID NO: 6            moltype = DNA  length = 1962
FEATURE                 Location/Qualifiers
source                  1..1962
                        mol_type = other DNA
                        organism = synthetic construct
SEQUENCE: 6
atgagtccca agacatcaaa accatttcac gtggagaacg acaccaccgc gggttattgg  60
tccaaccgtc cggaaaatac cctgccaccg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc ggcgggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962
```

```
SEQ ID NO: 7            moltype = DNA  length = 1962
FEATURE                 Location/Qualifiers
source                  1..1962
                        mol_type = other DNA
                        organism = synthetic construct
SEQUENCE: 7
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc ggcgggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                    1962

SEQ ID NO: 8            moltype = DNA  length = 1962
FEATURE                 Location/Qualifiers
source                  1..1962
                        mol_type = other DNA
                        organism = synthetic construct
SEQUENCE: 8
atgagtccca agacatcaaa accatttcac gtggagaacg acaccaccgc gggttattgg  60
tccaaccgtc cggaaaatac cctgccagtg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaaggccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacatg catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc ggcgggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
```

```
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 9            moltype = DNA  length = 1962
FEATURE                 Location/Qualifiers
source                  1..1962
                        mol_type = other DNA
                        organism = synthetic construct
SEQUENCE: 9
atgagtccca agacatcaaa accatttcac gtggagaacg acaccaccgc gggttattgg  60
tccaaccgtc cggaaaatac cctgccagtg ccggacatga tgggtgcgta catgcgtaat  120
caccegtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttctgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 10           moltype = DNA  length = 1962
FEATURE                 Location/Qualifiers
source                  1..1962
                        mol_type = other DNA
                        organism = synthetic construct
SEQUENCE: 10
atgagtccca agacatcaaa accatttcac gtggagaacg acaccaccgc gggttattgg  60
tccaaccgtc cggaaaatac cctgccagtg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacatg catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
```

```
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 11           moltype = DNA  length = 1962
FEATURE                 Location/Qualifiers
source                  1..1962
                        mol_type = other DNA
                        organism = synthetic construct
SEQUENCE: 11
atgagtccca agacatcaaa accatttcac gtggagaacg acaccaccgc gggttattgg  60
tccaaccgtc cggaaaatac cctgccagtg ccggacatga tgggtgcgta catgcgtaat  120
caccccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc ggcgggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 12           moltype = DNA  length = 1962
FEATURE                 Location/Qualifiers
source                  1..1962
                        mol_type = other DNA
                        organism = synthetic construct
SEQUENCE: 12
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgccccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaaggccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacatg catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
```

```
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 13          moltype = DNA  length = 1962
FEATURE                Location/Qualifiers
source                 1..1962
                       mol_type = other DNA
                       organism = synthetic construct
SEQUENCE: 13
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga aggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 14          moltype = DNA  length = 1962
FEATURE                Location/Qualifiers
source                 1..1962
                       mol_type = other DNA
                       organism = synthetic construct
SEQUENCE: 14
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
```

```
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                      1962

SEQ ID NO: 15          moltype = DNA  length = 1962
FEATURE                Location/Qualifiers
source                 1..1962
                       mol_type = other DNA
                       organism = synthetic construct
SEQUENCE: 15
atgagtccca agacatcaaa accatttcac gtggagaacg acaccaccgc gggttattgg  60
tccaaccgtc cggaaaatac cctgccagtg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat ttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                      1962

SEQ ID NO: 16          moltype = DNA  length = 1962
FEATURE                Location/Qualifiers
source                 1..1962
                       mol_type = other DNA
                       organism = synthetic construct
SEQUENCE: 16
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat ttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
gccatgttca tgccgcgtgc gaagggtgac cgtccgcacg ttgttccgga gggctgcact  1560
```

-continued

```
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                      1962

SEQ ID NO: 17          moltype = DNA  length = 1962
FEATURE                Location/Qualifiers
source                 1..1962
                       mol_type = other DNA
                       organism = synthetic construct
SEQUENCE: 17
atgagtccca agacatcaaa accatttcac gtggagaacg acaccaccgc gggttattgg  60
tccaaccgtc cggaaaatac cctgccagtg ccggacatga tgggtgcgta catgcgtaat  120
cgcccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaactgga attatgacaa cttgtgggat  360
atgtttcaag atgtgcaagc gctggagctc ccggagggct actcggttct ggacgagtat  420
cgccaactga atgacgctga tccgaattgg agcaaggccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacatg catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt accgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttctgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttccgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                      1962

SEQ ID NO: 18          moltype = DNA  length = 1962
FEATURE                Location/Qualifiers
source                 1..1962
                       mol_type = genomic DNA
                       organism = Paracoccus aminophilus
SEQUENCE: 18
atgagtccca agacatcaaa accatttcac gtggagaacg acaccaccgc gggttattgg  60
tccaaccgtc cggaaaatac cctgccagtg ccggacatga tgggtgcgta catgcgtaat  120
cacccgtacc cgggcaacca agtcgagggc cgcaaggcat ggattatcgg ctctggtatt  180
gcaggcctgg cggcggcgtt ttacctgatt cgcgatggtg gcatgaaagg tcaagacatc  240
accattttag atgcattgga cgtcactggc ggttccctgg acggcgcggg taatccggaa  300
gacgggtaca tcattcgtgg tggtcgggag atgaacttca attatgacaa cttgtgggat  360
atgtttcaag atgtgcaagc gctggagctc ccggagggct actcggttct ggacgagtat  420
cgccaactga atgacgctga tccgaattgg agcaagtccc gtctgatgca caatcagggt  480
gagatcagag atttcagcac ctttggtctg acgaaaccgc agcagtggga actcatcaga  540
ttgttgttga agcgcaaaga agacctggac gatctgacca ttgaagatta cttttcgccg  600
ggtttcttac aaagcaactt ttggtttctg tggcgttcta tgttcgcctt cgagaactgg  660
cagagcctgt tggagatgaa actctacacc catcgctttc tggattctat cgacggtttc  720
gcggatatgt cctgcctggt tttcccgaag tataatcagc atgatacctt cgttaaacct  780
ctggtggatc atctcaagaa gctgggggtg caagttcaat ttgcgacccg tgttagcgac  840
ctggagatga ctgaagatgc aggcaaacgt agcgtgaccg gcattctcgc cagcgttaac  900
ggtcaagaac atcgtatccc ggtagatgaa aaagatgtgg tgttcgctct gactggcagc  960
atgacggagg gaacggccta cggtgatatg gaccacgcac cagttatgga acgtggacgt  1020
tctgacccgg gtccggactc ggactgggca ttatggcaga accttgcggc taagagcccg  1080
atctttggca acccgaaaaa gttttacggc gacatcgata aatccatgtg ggaaagcggt  1140
acactgacgt gcaaaccgag cccactgacc gatcgtctga cggagctttc cgtgaacgac  1200
ccgtacagcg gtaagaccgt gaccggcggt atcatcacct ttaccgatag taactgggtg  1260
atgagcgtga cctgcaaccg tcagccgcat tttctgggcc aaccgaagga tgttctggtc  1320
ttgtgggtct atgcactgct tatggacaaa gacggaaaca aagtgaagaa gccgatgccg  1380
gcatgtaccg gccgcgaaat attggcggaa ttgtgtcacc acctaggcat cccggacgac  1440
cagttcgaag ctgtggctgc gaagaccaaa gttcgtctcg ctctgatgcc gtatattacc  1500
```

```
agcatgttca tgccgcgtgc gaagggtgac cgtccgcacg ttgttccgga gggctgcact  1560
aatctggcgc tgatgggtca gttcgttgag acggccaatg acatcgtgtt caccatggat  1620
tctagcattc gtaccgcgcg tattggtgtt tataccctgt tgggcctgcg taagcaggtt  1680
ccggacatca gcccggtcca gtatgatatc cgcacgctga ttaaagccgc gcgcacggtt  1740
aacaacaacc agccgtttcc gggcgagagg ctgttacacc gtctgcttgg taaaacgtat  1800
tacgcccata ttctgcctcc gctgccagat cgcacccaga ccacccgcga cgcggctgaa  1860
accgaattga aggccttcct cggcaccggt ggcactgcgt tagcagcggt tggtggttgg  1920
ctgcagcgtg tacgtgagga tctgaaagag cgcacccgta ag                     1962

SEQ ID NO: 19          moltype = AA  length = 654
FEATURE                Location/Qualifiers
source                 1..654
                       mol_type = protein
                       organism = synthetic construct
SEQUENCE: 19
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 20          moltype = AA  length = 654
FEATURE                Location/Qualifiers
source                 1..654
                       mol_type = protein
                       organism = synthetic construct
SEQUENCE: 20
MSPKTSKPFH VENDTTAGYW SNRPENTLPP PDMMGAYMRN HPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKARLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT AMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 21          moltype = AA  length = 654
FEATURE                Location/Qualifiers
source                 1..654
                       mol_type = protein
                       organism = synthetic construct
SEQUENCE: 21
MSPKTSKPFH VENDTTAGYW SNRPENTLPP PDMMGAYMRN HPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 22          moltype = AA  length = 654
FEATURE                Location/Qualifiers
source                 1..654
                       mol_type = protein
                       organism = synthetic construct
SEQUENCE: 22
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
```

-continued

```
QFEAVAAKTK VRLALMPYIT SMFMPRAAGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 23          moltype = AA  length = 654
FEATURE                Location/Qualifiers
source                 1..654
                       mol_type = protein
                       organism = synthetic construct
SEQUENCE: 23
MSPKTSKPFH VENDTTAGYW SNRPENTLPP PDMMGAYMRN RPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKARLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT AMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 24          moltype = AA  length = 654
FEATURE                Location/Qualifiers
source                 1..654
                       mol_type = protein
                       organism = synthetic construct
SEQUENCE: 24
MSPKTSKPFH VENDTTAGYW SNRPENTLPP PDMMGAYMRN HPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAAGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 25          moltype = AA  length = 654
FEATURE                Location/Qualifiers
source                 1..654
                       mol_type = protein
                       organism = synthetic construct
SEQUENCE: 25
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAAGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 26          moltype = AA  length = 654
FEATURE                Location/Qualifiers
source                 1..654
                       mol_type = protein
                       organism = synthetic construct
SEQUENCE: 26
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKARLMHNQG EIRDFSTFGL TKPQQWELIR  180
LLLKRKEDLD DLTIEDYFSP GFLQSNFWFL WRSMFAFENW QSLLEMKLYM HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAAGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 27          moltype = AA  length = 654
FEATURE                Location/Qualifiers
```

```
source                  1..654
                        mol_type = protein
                        organism = synthetic construct
SEQUENCE: 27
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FLGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 28           moltype = AA  length = 654
FEATURE                 Location/Qualifiers
source                  1..654
                        mol_type = protein
                        organism = synthetic construct
SEQUENCE: 28
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYM HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 29           moltype = AA  length = 654
FEATURE                 Location/Qualifiers
source                  1..654
                        mol_type = protein
                        organism = synthetic construct
SEQUENCE: 29
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAAGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 30           moltype = AA  length = 654
FEATURE                 Location/Qualifiers
source                  1..654
                        mol_type = protein
                        organism = synthetic construct
SEQUENCE: 30
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKARLMHNQG EIRDFSTFGL TKPQQWELIR  180
LLLKRKEDLD DLTIEDYFSP GFLQSNFWFL WRSMFAFENW QSLLEMKLYM HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 31           moltype = AA  length = 654
FEATURE                 Location/Qualifiers
source                  1..654
                        mol_type = protein
                        organism = synthetic construct
SEQUENCE: 31
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
```

```
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLKELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 32          moltype = AA  length = 654
FEATURE                Location/Qualifiers
source                 1..654
                       mol_type = protein
                       organism = synthetic construct
SEQUENCE: 32
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 33          moltype = AA  length = 654
FEATURE                Location/Qualifiers
source                 1..654
                       mol_type = protein
                       organism = synthetic construct
SEQUENCE: 33
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 34          moltype = AA  length = 654
FEATURE                Location/Qualifiers
source                 1..654
                       mol_type = protein
                       organism = synthetic construct
SEQUENCE: 34
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
QFEAVAAKTK VRLALMPYIT AMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 35          moltype = AA  length = 654
FEATURE                Location/Qualifiers
source                 1..654
                       mol_type = protein
                       organism = synthetic construct
SEQUENCE: 35
MSPKTSKPFH VENDTTAGYW SNRPENTLPV PDMMGAYMRN RPYPGNQVEG RKAWIIGSGI  60
AGLAAAFYLI RDGGMKGQDI TILDALDVTG GSLDGAGNPE DGYIIRGGRE MNWNYDNLWD  120
MFQDVQALEL PEGYSVLDEY RQLNDADPNW SKARLMHNQG EIRDFSTFGL TKPQQWELIR  180
LLLKRKEDLD DLTIEDYFSP GFLQSNFWFL WRSMFAFENW QSLLEMKLYM HRFLDSIDGF  240
ADMSCLVFPK YNQHDTFVKP LVDHLKKLGV QVQFATRVSD LEMTEDAGKR TVTGILASVN  300
GQEHRIPVDE KDVVFALTGS MTEGTAYGDM DHAPVLERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FPGQPKDVLV LWVYALLMDK DGNKVKKPMP ACTGREILAE LCHHLGIPDD  480
```

-continued

```
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654

SEQ ID NO: 36          moltype = AA  length = 654
FEATURE                Location/Qualifiers
source                 1..654
                       mol_type = protein
                       organism = Paracoccus aminophilus
SEQUENCE: 36
MSPKTSKPFH VENDTTAGYW SNRPENTLPV PDMMGAYMRN HPYPGNQVEG RKAWIIGSGI  60
AGLAAAFYLI RDGGMKGQDI TILDALDVTG GSLDGAGNPE DGYIIRGGRE MNFNYDNLWD  120
MFQDVQALEL PEGYSVLDEY RQLNDADPNW SKSRLMHNQG EIRDFSTFGL TKPQQWELIR  180
LLLKRKEDLD DLTIEDYFSP GFLQSNFWFL WRSMFAFENW QSLLEMKLYT HRFLDSIDGF  240
ADMSCLVFPK YNQHDTFVKP LVDHLKKLGV QVQFATRVSD LEMTEDAGKR SVTGILASVN  300
GQEHRIPVDE KDVVFALTGS MTEGTAYGDM DHAPVMERGR SDPGPDSDWA LWQNLAAKSP  360
IFGNPKKFYG DIDKSMWESG TLTCKPSPLT DRLTELSVND PYSGKTVTGG IITFTDSNWV  420
MSVTCNRQPH FLGQPKDVLV LWVYALLMDK DGNKVKKPMP ACTGREILAE LCHHLGIPDD  480
QFEAVAAKTK VRLALMPYIT SMFMPRAKGD RPHVVPEGCT NLALMGQFVE TANDIVFTMD  540
SSIRTARIGV YTLLGLRKQV PDISPVQYDI RTLIKAARTV NNNQPFPGER LLHRLLGKTY  600
YAHILPPLPD RTQTTRDAAE TELKAFLGTG GTALAAVGGW LQRVREDLKE RTRK        654
```